United States Patent [19]

Madara

[11] Patent Number: 5,459,068

[45] Date of Patent: Oct. 17, 1995

[54] MICROASSAY SYSTEM FOR ASSESSING TRANSMIGRATION OF PMN ACROSS EPITHELIA IN A SEROSAL-TO-MUCOSAL DIRECTION

[75] Inventor: James L. Madara, Winchester, Mass.

[73] Assignee: Brigham and Women's Hospital, Boston, Mass.

[21] Appl. No.: 152,898

[22] Filed: Nov. 17, 1993

Related U.S. Application Data

[63] Continuation-in-part of Ser. No. 748,349, Aug. 22, 1991, abandoned, which is a continuation-in-part of Ser. No. 677,388, Apr. 1, 1991, abandoned.

[51] Int. Cl.$^6$ ............... C12M 3/06; C12M 1/34; C12M 1/42
[52] U.S. Cl. ............... 435/287.1; 435/287.2; 435/287.91; 435/288.1
[58] Field of Search ............... 435/29, 30, 240.241, 435/284–286, 287, 291, 297–301, 310, 311, 817, 809; 422/101, 102; 204/153.12, 403, 415; 324/692

[56] References Cited

U.S. PATENT DOCUMENTS

| | | | |
|---|---|---|---|
| 4,686,190 | 8/1987 | Cramer et al. | 435/291 |
| 4,722,899 | 2/1988 | Hamaoka et al. | 435/172.2 |
| 5,026,649 | 6/1991 | Lyman et al. | 435/284 |
| 5,139,951 | 8/1992 | Butz et al. | 435/284 |

OTHER PUBLICATIONS

Arnaout et al., "Relative Contribution of the Leukocyte Molecules Mo1, LFA–1, and p. 150,95 (LeuM5) in Adhesion of Granulocytes and Monocytes to Vascular Endothelium Is Tissue– and Stimulus–Specific," *J. Cell. Physiol.* 137:305–309 (1988).

Arnaout et al., "Inhibition of Phagocytosis of Complement C3– or Immunoglobulin G–coated Particles and of C3bi Binding by Monoclonal Antibodies to a Monocyte–Granulocyte Membrane Glycoprotein (Mo1)," *J. Clin. Invest.* 72:171–179 (Jul. 1983).

Barak et al., "Fluorescence staining of the actin cytoskeleton in living cells with 7–nitrobenz–2–oxa–1, 3–diazole–phallacidin," *Proc. Natl. Acad. Sci. USA* 77:980–984 (Feb. 1980).

Barak et al., "In Vivo Staining of Cytoskeletal Actin by Autointernalization of Nontoxic Concentrations of Nitrobenzoxadiazole–Phallacidin," *J. Cell Biol.* 89:368–372 (May 1981).

Barrett et al., "Differing effects of apical and basolateral adenosiine on colonic epithelial cell line $T_{84}$," *Am. J. Physiol.* 256:C197–C203 (1989).

Borrebaeck, C., "Strategy for the production of human monoclonal antibodies using in vitro activated B cells," *J. Immunol. Methods* 123:157–165 (1989).

Cartwright et al., "Synergistic Action of Cyclic Adenosine Monophosphate– and Calcium–mediated Chloride Secretion in a Colonic Epithelial Cell Line," *J. Clin. Invest.* 76:1837–1842 (Nov. 1985).

Cereijido et al., "Polarized Monolayers Formed by Eipithelial Cells on a Permeable and Translucent Support," *J. Cell Biol.* 77:853–880 (1978).

Chadwick et al., "Production of Peptides Inducing Chemotaxis and Lysosomal Enzyme Release in Human Neutrophils by Intestinal Bacteria in Vitro and in Vivo," *Scand. J. Gastro.* 23:121–128 (1988).

Cooper, J. A., "Effects of Cytochalasin and Phalloidin on Actin," *J. Cell Biol.* 105:1473–1478 (Oct. 1987).

Cramer et al., "Transepithelial migration of human neutrophils: An in vitro model system," *Proc. Natl. Acad. Sci. USA* 77:4069–4073 (Jul. 1980).

(List continued on next page.)

*Primary Examiner*—William H. Beisner
*Attorney, Agent, or Firm*—Sterne, Kessler, Goldstein & Fox

[57] ABSTRACT

A microassay system for the analysis of polymorphonuclear leukocyte transmigration across epithelia in the physiological direction. This assay also allows for the rapid analysis of a series of monolayers.

9 Claims, 13 Drawing Sheets

OTHER PUBLICATIONS

Cramer et al., "Effect of Human Serum and Some of Its Components on Neutrophil Adherence and Migration across an Epithelium," *J. Cell Biol.* 102:1868–1877 (May 1986).

Critchlow et al., "Requirements for Restitution of the Surface Epithelium of Frog Stomach After Mucosal Injury," *Gastroenterology* 88:237–249 (1985).

Dana et al., "Deficiency of a Surface Membrane Glycoprotein (Mo1) in Man," *J. Clin. Invest.* 73:153–159 (Jan. 1984).

van Deventer et al., "Intestinal Endotoxemia: Clinical Significance," *Gastroenterology* 94:825–831 (1988).

Dharmsathaphorn et al., "A human colonic tumor cell line that maintains vectorial electrolyte transport," *Am. J. Physiol.* 246:G204–G208 (1984).

Dharmsathaphorn et al., "Vasocactive Intestinal Polypeptide-induced Chloride Secretion by a Colonic Epithelial Cell Line," *Clin. Invest.* 75:462–471 (Feb. 1985).

Dharmsathaphorn & Pandol, "Mechanism of Chloride Secretion Induced by Carbachol in a Colonic Epithelial Cell Line," *J. Clin. Invest. 77:348–354 (Feb. 1986).*

Dharmsathaphorn & Madara, "Established Intestinal Cell Lines as Model Systems for Electrolyte Transport Studies," *Methods in Enzymology* 192:354–389 (1990).

Donowitz & Welsh, "Regulation of Mammalian Small Intestinal Electrolyte Secretion," in: *Physiology of the Gastrointestinal Tract*, Johnson, L. (Ed.), pp. 1351–1388 (1987).

Duffey et al., "Regulation of epithelial tight junction permeability by cyclic AMP", *Nature* 294:451–453 (1981).

Evans et al., "Transepithelial Chemotaxis of Rat Peritoneal Exudate Cells," *Br. J. Exp. Path.* 64:644–654 (1983).

Finley & Smith, "Stimulation of Chloride Secretion by N-Formyl-Methionylleucylphenylalanine (FMLP) in Rabbit Ileal Mucosa," *J. Physiol.* 417:403–419 (1989).

Goodman, "Immunogenicity & Antigenic Specificity," in: Basic & Clinical Immunology, Fudenberg et al. (eds), Lange Medical Publ., Calif., pp. 32–40 (1976).

Guthrie et al., "Priming of Neutrophils For Enhanced Release of Oxygen Metabolites by Bacterial Lipopolysaccharide," *J. Exp. Med.* 160:1656–1671 (Dec. 1984).

Hamaguchi & Mabuchi, "Effects of Phalloidin Microinjection and Localization of Fluorescein-Labeled Phalloidin in Living Sand Dollar Eggs," *Cell Motility* 2:103–113 (1982).

Hammerling et al., "Production of Antibody-Producing Hybridomas in the Rodent Systems," in: Monoclonal Antibodies and T-Cell Hybridomas, Elsevier, N.Y., pp. 563, 565–587 (1981).

Hawker et al., "Electrolyte Transport Across Colonic Mucosa from Patients with Inflammatory Bowel Disease," *Gastroenterology* 79:508–511 (1980).

Hecht et al., "*Clostridium difficile* Toxin A Perturbs Cytoskeletal Structure and Tight Junction Permeability of Cultured Human Intestinal Epithelial Monolayers," *J. Clin. Invest.* 82:1516–1524 (Nov. 1988).

Hellstrom et al., "Immunological Approaches to Tumor Therapy: Monoclonal Antibodies, Tumor Vaccines, and Anti-Idiotypes," in: Covalently Modified Antigens & Antibodies in Diagnosis & Therapy, Quash & Rodwell (eds.), vol. 12, pp. 1–37, (1989).

Henson & Oades, "Stimulation of Human Neutrophils by Soluble and Insoluble Immunobulin Aggregates," *J. Clin. Invest.* 56:1053–1061 (Oct. 1975).

Horii et al., "Neutrophilic nodules in the intestinal walls of Japanese monkeys associated with the neutrophil chemotactic activity of larval extracts and secretions of *Oesophagostomum aculeatum*," Res. Vet. Sci. 38:115–119 (1985).

Howard & Oresajo, "The Kinetics of Chemotactic Peptide-induced Change in F-Actin Content, F-Actin Distribution and the Shape of Neutrophils," *J. Cell Biol.* 101:1078–1085 (Sep. 1985).

Hsu et al., "Cloning of cDNAs for human aldehyde dehydrogenases 1 and 2," *Proc. Natl. Acad. Sci. USA* 82:3771–3775 (Jun. 1985).

Huott et al., "Mechanism of Action of *Escherichia coli* Heat Stable Enterotoxin in a Human Colonic Cell Line," *J. Clin. Invest.* 82:514–523 (Aug. 1988).

Jacobson, H. R., "Altered permeability in the proximal tubule response to cyclic AMP," *Am. J. Physiol.* 236:F71–F79 (1979).

Jorgensen et al., "Identification of a $Na^+$, $K^+$, $Cl^-$—Cotransport Protein of Mr 34000 From Kidney By Photolabeling with [$^3$H]Bumethanide," *Biochimica et Biophysics Acta* 775:105–110 (1984).

Kam et al., "Cloning sequencing and chromosomal localization of human term placental alkaline phosphatase cDNA," *Proc. Natl. Acad. Sci. USA* 82:8715–8719 (Dec. 1985).

Karayalcin et al., "Hydrogen Peroxide Stimulates Rat Colonic Prostaglandin Production and Alters Electrolyte Transport," *J. Clin. Invest.* 86:60–68 (Jul. 1990).

Köhler & Milstein, "Continuous cultures of fused cells secreting antibody of predefined specificity," *Nature* 256:495–497 (Aug. 7, 1975).

Köhler & Milstein, "Derivation of specific antibody-producing tissue culture and tumor lines by cell fusion," *Eur. J. Immunol.* 6:511–519 (1976).

Köhler et al., "Fusion between immunoglobulin-secreting and nonsecreting myeloma cell lines," *Eur. J. Immunol.* 6:292–295 (1976).

Kostyo & Knobil, "The Effect of Growth Hormone on the In Vitro Incorporation of Leucine-2-$C^{14}$ into the Protein of Rat Diaphragm," *Endocrinology* 65:395–401 (1959).

Kumar et al., "The histopathologic spectrum of acute self-limited colitis (acute infectious-type colitis)," *Am. J. Surg. Path.* 6:523–529 (Sep. 1982).

Liu et al., "Complete amino acid sequences of two protease inhibitors in the venom of *Bungarus fasciatus*,"*Int. J. Pept. Prot. Res.* 21:209–215 (1983).

Luscinskas et al., "Endothelial-Leukocyte Adhesion Molecule-1-Dependent and Leukocyte (CD11/CD18)-Dependent Mechanisms Contribute to Polymorphonuclear Leukocyte Adhesion to Cytokine-Activated Human Vascular Endothlium," *J. Immunol.* 142:2257–2263 (Apr. 1, 1989).

Madara et al., "Occluding Junction Structure-Function Relationships in a Cultured Epithelial Monolayer," *J. Cell. Biol.* 101:2124–2133 (Dec. 1985).

Madara et al., "Effects of Cytochalasin D on Occluding Junctions of Intestinal Absorptive Cells: Further Evidence That the Cytoskeleton May Influence Paracellular Permeability and Junctional Charge Selectivity," *J. Cell Biol.* 102:2125–2136 (Jun. 1986).

Madara & Pappenheimer, "Structural Basis for Physiological Regulation of Paracellular Pathways in Intestinal Epithelia," *J. Membr. Biol.* 100:149–164 (1987).

Madara et al., "5'-Adenosine Monophosphate Is the Neutrophil-derived Paracrine Factor that Elicits Chloride Secretion from T84 Intestinal Epithelial Cell Monolayers," *J. Clin. Invest.* 91:2320–2325 (May 1993).

Migliorisi et al., "Differences in the Ability of Neutrophils and Monocytes to Traverse Epithelial Occluding Junctions," *J. Leuk. Biol.* 44:485–492 (1988).

Milks et al., "Epithelial Permeability and the Transepithelial Migration of Human Neutrophils," *J. Cell Biol.* 96:1241–1247 (May 1983).

Misfeldt et al., "Transepithelial transport in cell culture," *Proc. Natl. Acad. Sci. USA* 73:1212–1216 (Apr. 1976).

Naccache et al., "Specificity of the Effect of Lipoxygenase Metabolites of Arachidonic Acid on Calcium Homeostasis in Neutrophils," *J. Biol. Chem.* 257:8608–8611 (Aug. 10, 1982).

Nash et al., "Activation of Polymorphonuclear Leukocytes (PMN) Stimulates Chloride Secretion in a Model Intestinal Epithelium," 91st Annual Meeting of the American Gastroenterological Assoc. & Digestive Disease Week, San Antonio, Tex., USA, May 12–18, 1990, *Gastroenterology* 98:A550 (1990), Abstract only.

Nash et al., "The Selective and Superoxide–Independent Disruption and Intestinal Epithelial Tight Junctions During Leukocyte Transmigration," *Lab. Invest.* 59:531–537 (1988).

Nash et al., "In Vitro Model of Intestinal Crypt Abscess," *J. Clin. Invest.* 87:1474–1477 (Apr. 1991).

Nash et al., "Effects of PolyMorphonuclear Leukocyte Transmigration on the Barrier Function of Cultured Intestinal Epithelial Monolayers," *J. Clin. Invest.* 80:1104–1113 (Oct. 1987).

Nathan, C., "Neutrophil Activation on Biological Surfaces," *J. Clin. Invest.* 80:1550–1560 (Dec. 1987).

Nathan et al., "Cytokine–induced Respiratory Burst of Human Neutrophils: Dependence on Extracellular Matrix Proteins and CD11/CD18 Integrins," *J. Cell Biol.* 109:1341–1349 (Sep. 1989).

Oike et al., "A Mapping Technique for Probing the Structure of Proteoglycan Core Molecules," *J. Biol. Chem.* 257:9751–9758 (Aug. 25, 1982).

Omann et al., "Signal Transduction and Cytoskeletal Activation in the Neutrophil," *Physiol. Rev.* 67:285–322 (Jan. 1987).

Parkos et al., "Regulation of the Oxidative Response of Human Granulocytes to Chemoattractants," *J. Biol. Chem.* 260:6541–6547 (Jun. 1985).

Parkos et al., "Neutrophil Migration across a Cultured Intestinal Epithelium," *J. Clin. Invest.* 88:1605–1612 (Nov. 1991).

Parsons et al., "The Effect of Neutrophil Migration and Prolonged Neutrophil Contact on Epithelial Permeability," *Am. J. Pathol.* 129:302–312 (Nov. 1987).

Pennica et al., "Cloning and expression of human tissue–type plasminogen activator cDNA in *E. coli*," *Nature* 301:214–221 (Jan. 20, 1983).

Phillips et al., "Phallacidin prevents thrombin–induced increases in endothelial permeability to albumin," *Am. J. Physiol* 257:C562–C567 (1989).

Pick & Keisari, "A simple colorimetric method for the measurement of hydrogen peroxide produced by cells in culture," *J. Immunol. Meth.* 38:161–170 (1980).

Pick & Mizel, "Rapid microassays for the measurement of superoxide and hydrogen peroxide production by macrophages in culture using an automatic enzyme immunoassay reader," *J. Immunol. Meth.* 46:211–226 (1981).

Potocnjak et al., "Inhibition of Idiotype–Anti–Idiotype Interaction for Detection of a Parasite Antigen: A New Immunoassay," *Science* 215:1637–1639 (Mar. 26, 1982).

Ritz et al., "A monoclonal antibody to human acute lymphoblastic leukaemia antigen," *Nature* 283:583–585 (1980).

Rudinger, J., "Characteristics of the amino acids as components of a peptide hormone sequence," in: *Peptide Hormones*, Parsons (ed.), U Park Press, Baltimore, 1–7 (1976).

Ruoslahti, E., "Integrins," *J. Clin. Invest.* 87:1–5 (Jan. 1991).

Serhan et al., "Lipoxin Formation during Human Neutrophil–Platelet Interactions: Evidence for the Transformation of Leukotriene $A_4$ by Platelet 12–Lipoxygenase in Vitro," *J. Clin. Invest.* 85:772–780 (Mar. 1990).

Shapiro et al., "Stabilization of F–Actin Prevents cAMP–Elicited $Cl^-$ Secretion in T84 Cells," *J. Clin. Invest.* 87:1903–1909 (Jun. 1991).Smith et al., "Recognition of an Endothelial Determinant for CD18–dependent Human Neutrophil Adherence and Transendothelial Migration," *J. Clin. Invest.* 82:1746–1756 (Nov. 1988).

Smolen, J. E., "Characteristics and Mechanisms of Secretion by Neutrophils," in: The Neutrophil: Cellular Biochemistry & Physiology, pp. 23–61 (1989).

Stelzner et al., "Role of Cyclic Adenosine Monophosphate in the Induction of Endothelial Barrier Properties," *J. Cell. Physiol.* 139:157–166 (1989).

Suzuki et al., "Complete amino acid sequence of human vitronectin deduced from cDNA. Similarity of cell attachment sites in vitronectin and fibronectin," *Embo J.* 4:2519–2524 (1985).

Tamai et al., "Monochloramine, A Neutrophil–Derived Oxidant, Stimulates Secretion and Increases Cytosolic $Ca^{2+}$ in T–84 Cultured Colonic Cells," *Gastroenterology* 98:A557–A558 (May 1990). Abstract only.

Tamai et al., "Scavenging Effect of 5–aminosalicylic acid on neutrophil–derived oxidants," *Biochem. Pharm.* 41:1001–1006 (1991).

Tamai et al., "Monochloramine, a Neutrophil–Derived Oxidant, Stimulates Rat Colonic Secretion," *J. Pharmacol. & Exp. Therapeutics* 257:887–894 (1991).

Walter et al., "Cloning of the human estrogen receptor cDNA," *Proc. Natl. Acad. Sci. USA* 82:7889–7893 (Dec. 1985).

Wands & Zurawski, "High Affinity Monoclonal Antibodies to Hepatitis B Surface Antigen ($HB_8$ Ag) Produced by Somatic Cell Hybrids," *Gastroenterology* 80:225–232 (1981).

Watson, J. D., "The Genetic Code," in: Molecular Bio. of the Gene, 3rd Ed., W. A. Benjamin, Inc., Menlo, Calif., pp. 347–377 (1976).

Weymer et al., "Chloride Secretory Mechanism Induced by Prostaglandin $E_1$ in a Colonic Epithelial Cell Line," *J. Clin. Invest.* 76:1828–1836 (Nov. 1985).

White et al., "Mast Cell Secretagogues," *Biochemistry of the Acute Allergic Reactions: Fifth International Symposium*, pp. 83–101 (1989).

Yardley, J. H., in: Recent developments in the therapy of inflammatory bowel disease, Myerhoff (eds.), Center for Digestive Disease at Johns Hopkins, Baltimore, Md., pp. 16–20 (1986).

Yardley et al., in: The gastrointestinal Tract, J. H. Yardley & B. C. Morrison (eds.), Williams & Wilkins Co., Baltimore, Md., p. 57 (1977).

Zurier et al., "Cytochalasin B: Effect on Lysosomal Enzyme Release from Human Leukocytes," *Proc. Natl. Acad. Sci. USA* 70:844–848 (Mar. 1973).

control-apical control-bl cAMP-apical cAMP-bl

MICROASSAY SYSTEM FOR ASSESSING TRANSMIGRATION OF PMN ACROSS EPITHELIA IN A SEROSAL-TO-MUCOSAL DIRECTION

STATEMENT AS TO RIGHTS TO INVENTIONS MADE UNDER FEDERALLY-SPONSORED RESEARCH AND DEVELOPMENT

This invention was made with government support under Grant #PO1 DK 33506 awarded by the National Institutes of Health. The U.S. government has certain rights in this invention.

CROSS-REFERENCE TO RELATED APPLICATIONS

This is a continuation-in-part of application Ser. No. 07/748,349, filed Aug. 22, 1991, now abandoned, which is a continuation-in-part of application Ser. No. 07/677,388, filed Apr. 1, 1991, now abandoned.

FIELD OF THE INVENTION

The present invention relates generally to the fields of hematology and immunology. The invention specifically relates to chloride secretion of intestinal epithelial cells. The invention also relates to the use of a microassay system capable of detecting chloride secretion. Specifically, the microassay allows the rapid assessment of a series of monolayers for the presence (and magnitude) of a short circuit current that is indicative of electrogenic $Cl^-$ secretion. An additional aspect of the invention is a microassay system designed for the analysis of polymorphonuclear leukocyte transmigration across epithelia in the physiological direction.

RELATED ART

Although inflammatory diseases of the intestine are, as a group, diverse, many of these diseases express similar morphologic features. For example, in active intestinal inflammation, polymorphonuclear leukocytes (PMN.'s) characteristically migrate across the epithelium to collect in crypts, a diagnostic feature, termed a "crypt abscess," which is used clinically to evaluate the level of activity of various inflammatory bowel diseases (Kumar et al., *Am. J. Surg. Path* 6:523–529 (1982); Yardley, J. H., In Recent developments in the therapy of inflammatory bowel disease, Myerhoff Center for Digestive Disease at Johns Hopkins, Baltimore, Md. 3–9 (1986)). Using the T84 crypt-like intestinal epithelial cell line (Dharmsathaphorn et al., *Am. J. Physiol.* 246:G204–G208 (1984); Madara et al., *J. Cell Biol.* 101:2124–2133 (1985); Dharmsathaphorn et al., *Methods in Enzymology* 192:354–389 (1990)), and purified PMN, this transmigratory event was previously modeled (Nash et al., *J. Clin. Invest.* 80:1104–1113 (1987)).

Although the degree of PMN trasmigration into intestinal crypts and formation of crypt abscesses is indicative of disease severity (Yardley et al., *In the Gastrointestinal Tract*, Williams & Wilkins, Baltimore, p. 57 (1977)), little is known concerning the mechanisms by which PMN's migrate across epithelia.

Present within the intestinal and crypt lumen are bacterial products, such as lipopolysaccharide (LPS) (at μg/ml concentrations) (van Deventer et al., *Gastroenterology* 94:825–831 (1988)) and n-formylated peptides (at μM concentrations) (Chadwick et al., *Scand. J. Gastro.* 23:121–128 (1988)). As modeled by For-MLF (N-formyl methionyl leucyl phenylalanine), N-formylated peptides induce both respiratory burst activity (Omann et al., *Physiological Reviews* 67:285–322 (1987)) and degranulation (Smolen, J. E., *In The Neutrophil: Cellular Biochemistry and Physiology* 23–62 (1989)) in PMN -responses which may be enhanced when PMN's are "primed" by LPS (Guthrie et al., *J. Exp. Med.* 160:1656–1671 (1984)), as would be the case in the intestinal lumen. Thus, the known conditions in the intestinal lumen should affect the metabolic state of PMN's within crypt abscesses; specifically, inducing PMN's to generate a complex array of reactive oxygen species, proteases, lipoxygenase, and other products that might influence the functional state of crypt epithelial cells.

A recent, extensively used, system for studying electrogenic $Cl^-$ secretion (Dharmsathaphorn et al., *American Journal of Physiology* 246:G204–G208 (1984)) has a number of disadvantages. The filters upon which the cells are to be plated are first coated with collagen. The method of coating the collagen requires coating, drying, and rehydrating for about 6–10 hours over the course of 2 days and necessitates multiple manipulations.

Another drawback to the assay currently used to assess $Cl^-$ secretion and PMN transmigration is the use of cumbersome Ussing chambers. The construction and design of the Ussing chambers is such that one can only perform about 12 assays per day, since the time required to tear down, clean, and reset the chamber is considerable. This method also requires monolayers sufficient to cover a 2 $cm^2$ area.

When assessing the transmigration of PMN's, the assay has the added drawback of not assessing the transmigration in the physiological direction (serosal to mucosal). Rather, the system only permits the study of PMN transmigration across epithelia in the mucosal to serosal direction.

SUMMARY OF THE INVENTION

Accordingly, the present invention is directed to a microassay that is useful for detecting chloride secretion in intestinal epithelial cells. Specifically, the novel microassay allows one to rapidly assess a series of monolayers for the presence (and magnitude) of a short-circuit current (Isc), which is indicative of electrogenic $Cl^-$ secretion.

The microassay allows one to perform 10–20 times more assays in a day than the previous system. Additionally, the inventor's method of coating the filter, by virtue of eliminating the need to coat, dry, rehydrate, etc., significantly reduces the time required for that step.

This novel microassay permits the rapid and economical screening of agents capable of stimulating or blocking electrogenic chloride secretion of epithelial cells. The discovery of such agents provides for advances in the therapy of acute inflammation of the intestine.

The microassay may also be adapted to permit the study of PMN transmigration in the physiological direction. Until the inventor's creation of this microassay, PMN transmigration had not been studied in the physiological direction. As demonstrated by the inventor in the examples presented herein, such studies are imperative, since their results reveal that parameters, such as efficiency of transmigration, are affected by the orientation of the assay (more efficient in "physiological" direction).

In addition to the novel microassay system, the inventor has successfully identified a neutrophil-derived secretagogue (NDS) capable of inducing an increase in Isc response when applied to the luminal surface of epithelial monolayers. This is the first instance of a NDS capable of acting at the apical membrane, that does not require Ca, cGMP, or cAMP signal to express its activity.

The identification of the NDS permits the screening of inhibitory agents that may be used therapeutically in attenuating the secretory diarrhea associated with intestinal inflammation. The ability of NDS to act directly on $Cl^-$ channels (apically located) suggests treatments for illnesses, such as cystic fibrosis, where patients have normal $Cl^-$ channels that are defectively regulated.

It is an object of the present invention, then, to provide a microassay useful for the screening of agents that may be used therapeutically in attenuating the secretory diarrhea associated with intestinal inflammation. The present invention thus provides an important advance in the study and therapy of active intestinal diseases, such as ulcerative colitis, Crohn's disease, and infectious enterocolitis.

NDS induces an Isc response and is only active when applied to the luminal surface of monolayers and does not require PMN-epithelial contact. Additionally, the NDS activity is not secondary to the respiratory burst products $O_2$ or $H_2O_2$ and is not a myeloperoxidase product. The NDS coupled with the novel microassay makes possible new assays and treatments for secretory diarrhea and intestinal inflammation.

Accordingly, in one embodiment, the current invention provides a method of assessing a series of monolayers for a short-circuit current (Isc), comprising: (a) coating ring-supported polycarbonate filters with a viscous solution of collagen; (b) plating epithelial cells onto the coated inserts; (c) maintaining the inserts in welled culture plates until electrical stability is achieved; and (d) installing electrodes in said welled culture plate via agar bridges, and installing a voltage clamp in said welled culture plate thereby creating a microassay capable of detecting electrogenic $Cl^-$ secretion.

Also provided is a method of determining the ability of a factor to modulate chloride secretion of epithelial cells, comprising: (a) coating ring-supported polycarbonate filters with a viscous solution of collagen; (b) plating epithelial cells onto the coated inserts; (c) maintaining the inserts in welled culture plates until electrical stability is achieved; and (d) placing electrodes via agar bridges, and placing a voltage clamp thereby creating a microassay capable of detecting electrogenic $Cl^-$ secretion; (e) applying NDS or polymorphonuclear cells to the mucosal bath compartment, so that the NDS would produce an electrogenic $Cl^-$ secretion from the epithelial cells; and then (f) assessing the ability of the factor to modulate the $Cl^-$ secretory response of the epithelial cells.

In a preferred embodiment, the present invention relates to an apparatus for assessing transmigration of polymorphonuclear leukocytes (PMN's) across epithelia in a serosal-to-mucosal direction, comprising:

(a) a culture plate having an upper surface and a plurality of individual wells, each well having an internal surface;

(b) at least one insert that is removably disposed within said well of said culture plate, said insert comprising:
   (i) a hollow cylinder having an open top end, an open bottom end having a bottom edge and an inner diameter, and an inner and an outer surface;
   (ii) means for suspending said cylinder placed between said top end of said cylinder and said upper surface of said culture plate;
   (iii) a filter having a first and second surface;
   (iv) a layer of collagen as a viscous solution provided on said first surface of said filter whereby a cell monolayer can be grown on said layer of collagen;
   (v) a ring having approximately the same diameter as said bottom end of said cylinder, said filter being attached to said ring and said bottom edge of said cylinder so that said first surface of said filter is in communication with said ring and said second surface of said filter is in communication with said bottom edge of said cylinder;

(c) an internal serosal reservoir bound by said inner surface of said cylinder, and said second surface of said filter;

(d) a first means for passing current and a first means for recording voltage disposed within said internal serosal reservoir above said second surface of said filter;

(e) an external mucosal reservoir bound by said inner surface of said well, said external surface of said cylinder, said ring, and said first surface of said filter; and (f) a second means for passing current and a second means for recording voltage disposed within said external mucosal reservoir below said first surface of said filter.

Another embodiment of the current invention provides a method of assessing a series of monolayers for PMN transmigration across the epithelia in the physiological direction, comprising: (a) gluing polycarbonate rings holding filters, having the same diameter as the insert base, to the bottom of said inserts; (b) coating the inverted ring-supported polycarbonate filter with a viscous collagen solution; (c) plating epithelia cells onto the coated inserts; (d) righting the insert into the well of the culture plate and maintaining the culture plate until electrical stability is achieved; and (e) installing electrodes via agar bridges and placing a voltage clamp so as to create a microassay capable of assessing PMN transmigration in the physiological direction.

These and other non-limiting embodiments of the present invention will be apparent to those skilled in the art from the following detailed description of the invention.

BRIEF DESCRIPTION OF THE FIGURES

In FIG. 12 A, T84 monolayers are shown growing in the conventional configuration in which PMN's are layered, by gravity on ("mucosal") surface of the monolayer. In FIG. 12 B, inverted monolayers for use in studies of PMN transmigration in the physiologically relevant (serosal-to-mucosal) direction are shown. Antibodies are depicted as Y in the upper chambers of 12 A and 12 B. The letters I and E correspond to agar bridges interfacing with current passing or voltage sensitive electrodes in inner (1) or outer (2) reservoirs.

DETAILED DESCRIPTION OF THE PREFERRED EMBODIMENTS

In the following description, reference will be made to various methodologies known to those skilled in the art of molecular biology and immunology. Publications and other materials setting forth such known methodologies to which reference is made are incorporated herein by reference in their entireties as though set forth in full.

Figure 12B:
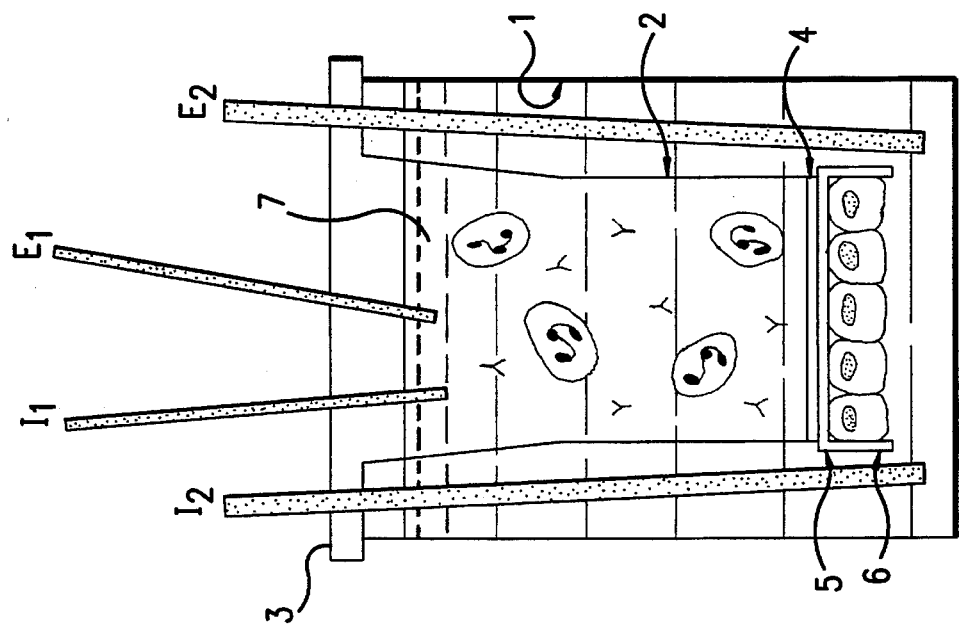
FIGS. 12A–B show a simple efficient system for electrical assays of PMN transmigration across T84 monolayers.
Figure 12A:
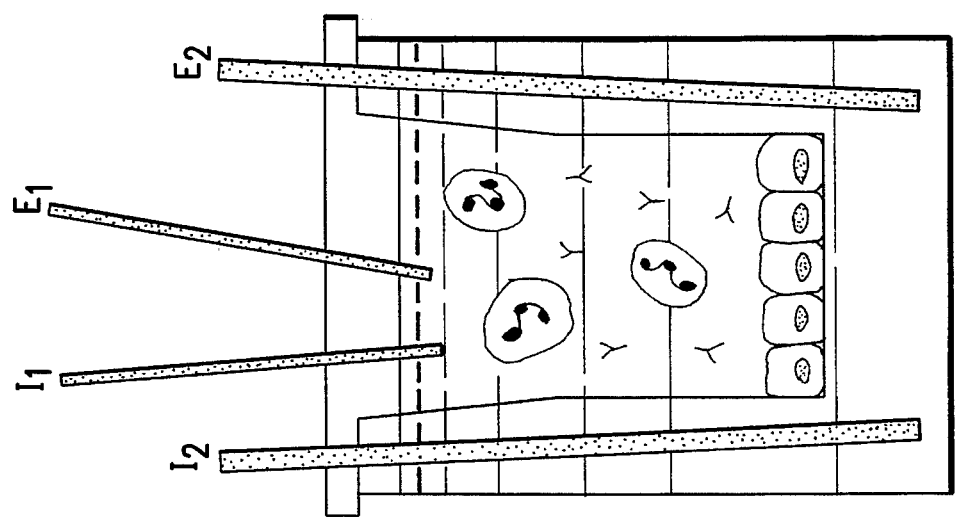

The present invention is directed to an apparatus for detecting Cl⁻ secretion as shown in FIG. 12 B comprising: (a) a culture plate having an upper surface, and a plurality of individual wells each well having an internal surface (1); (b) at least one insert that is removably disposed within a well of the culture plate, said insert comprising: (i) a hollow cylinder (2) having an open top end, an open bottom end having a bottom edge and an inner diameter, and an inner and an outer surface; (ii) means (3) for suspending the cylinder placed between the top end of the cylinder and the upper surface of the culture plate; (iii) a filter (4) having a first and second surface; (iv) a layer of collagen (5) in the form of a viscous solution provided on the first surface of the filter whereby a cell monolayer can be grown on said layer of collagen; (v) a ring (6) having approximately the same diameter as the bottom end of the cylinder, the filter being attached to the ring and the bottom edge of the cylinder so that the first surface of the filter is in communication with the ring and the second surface of the filter is in communication with the bottom edge of the cylinder; (c) an internal serosal reservoir (7) bound by the inner surface of the cylinder, and the second surface of the filter; (d) a first means ($I_1$) for passing current and a first means ($E_1$) for recording voltage disposed within the internal serosal reservoir above the second surface of the filter; and (e) an external mucosal reservoir (8) bound by the inner surface of the well, the external surface of the cylinder, the ring, and the first surface of the filter; (f) a second means ($I_2$) for passing current and a second means ($E_2$) for recording voltage disposed within the external mucosal reservoir below the first surface of the filter.

DEFINITIONS

By "substantially pure" is meant any molecule, or any gene encoding any such molecule, that is essentially free of other antigens or genes, respectively, or of other contaminants with which it might normally be found in nature, and, as such, exists in a form not found in nature.

By "functional derivative" is meant the "fragments," "variants," "analogues," or "chemical derivatives" of a molecule.

A "variant" of such molecule is meant to refer to a naturally occurring molecule substantially similar to either the entire molecule, or a fragment thereof.

An "analogue" of a molecule is meant to refer to a non-natural molecule substantially similar to either the entire molecule or a fragment thereof.

A molecule is said to be "substantially similar" to another molecule if both molecules possess a similar activity. Substantially similar polypeptide molecules will possess a similar biological activity. Thus, provided that two molecules possess a similar activity, they are considered variants, as that term is used herein, even if one of the molecules contains additional amino acid residues not found in the other, or if the sequence of amino acid residues is not identical.

As used herein, a molecule is said to be a "chemical derivative" of another molecule if it contains additional chemical moieties not normally a part of the molecule. Such moieties may improve the molecule's solubility, absorption, biological half life, etc. The moieties may, alternatively, decrease the toxicity of the molecule, eliminate, or attenuate any undesirable side effect of the molecule, etc. Moieties capable of mediating such effects are disclosed, for example, in *Remington's Pharmaceutical Sciences*, 16th ed., Mack Publishing Co., Easton, Pa. (1980).

Similarly, "functional derivative" is meant to include "fragments," variants," or "analogues", that may be "substantially similar" in activity.

Thus, as used herein, "neutrophil-derived secretagogue" (NDS) is also meant to include any functional derivative, fragments, variants, analogues, or chemical derivatives that are substantially similar to NDS and that possess similar activity.

"Receptor" as used herein is meant to include molecules that are expressed on the cell surface that are capable of binding to NDS or a functional or chemical derivative thereof.

Antibodies according to the present invention can be prepared by any of a variety of methods. For example, cells releasing the secretagogue or expressing the NDS receptor, or a functional derivative thereof, can be administered to an animal in order to induce the production of sera containing polyclonal antibodies that are capable of binding the secretagogue or the receptor.

In a preferred method, antibodies according to the present invention are monoclonal antibodies. Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 1976); Hammerling et al., In: *Monoclonal Antibodies and T-Cell Hybridomas*, Elsevier, N.Y., pp. 563–681 (1981)). In general, such procedures involve immunizing an animal with the NDS antigen. The splenocytes of such animals are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands, J. R., et al. (*Gastroenterology* 80:225–232 (1981). The hybridoma cells obtained through such a selection are then assayed to identify clones that secrete antibodies capable of binding to NDS.

Antibodies according to the present invention also may be polyclonal, or, preferably, region specific polyclonal antibodies.

The term "detecting" is intended to include determining the presence or absence of a substance or quantifying the amount of a substance. The term thus refers to the use of the materials, compositions, and methods of the present invention for qualitative and quantitative determinations.

The isolation of other hybridomas secreting monoclonal antibodies of the same specificity as those described herein can be accomplished by the technique of anti-idiotypic screening. Potocmjak, et at., *Science* 215:1637 (1982). Briefly, an anti-idiotypic antibody is an antibody that recognizes unique determinants present on the antibody produced by the clone of interest. The anti-idiotypic antibody is prepared by immunizing an animal of the same strain used as the source of the monoclonal antibody with the monoclonal antibody of interest. The immunized animal will recognize and respond to the idiotypic determinants of the immunizing antibody by producing antibody to these idiotypic determinants (anti-idiotypic antibody).

For replication, hybrid cells may be cultivated both in vivo and in vitro. High in vivo production makes this the currently preferred method of culture. Briefly, cells from the individual hybrid strains are injected intraperitoneally into pristane-primed BALB/c mice to produce ascites fluid containing high concentrations of the desired monoclonal antibodies. Monoclonal antibodies of isotype IgM or IgG can be purified from cultured supernatants using column chromatography methods well known to those of skill in the art.

NDS or NDS receptors may be isolated in substantially pure form by means of antibodies. The substantially pure NDS may in turn be used to detect or measure antibody to the NDS in a sample. Thus, one embodiment of the present invention comprises a method of detecting the presence or amount of antibody to NDS in a sample, comprising contacting said sample containing said antibody to the NDS with detectably labeled NDS, and detecting said label. It will be appreciated that immunoreactive fractions and immunoreactive analogues of the NDS or NDS receptor also may be used. By the term "immunoreactive fraction" is intended any portion of the NDS molecule that demonstrates an equivalent immune response to an antibody directed against the NDS. By the term "immunoreactive analogue" is intended a protein that differs from the NDS by one or more amino acids, but that demonstrates an equivalent immunoresponse to an antibody of the invention.

Cloning of the Neutrophil-derived Secretagogue Receptor

Any of a variety of procedures may be used to clone the neutrophil-derived secretagogue receptor gene. One such method entails analyzing a shuttle vector library of cDNA inserts (derived from a neutrophil-derived secretagogue receptor expressing cell) for the presence of an insert that contains the neutrophil-derived secretagogue receptor gene. Such an analysis may be conducted by transfecting cells with the vector and then assaying for NDS receptor expression. The preferred method for cloning this gene entails determining the amino acid sequence of the NDS receptor molecule. To accomplish this task, the NDS receptor may be purified and analyzed by automated sequentors. Alternatively, the molecule may be fragmented as with cyanogen bromide, or with proteases such as papain, chymotrypsin, or trypsin (Oike, Y. et al., *J. Biol. Chem* 257:9751–9758 (1982); Liu, C. et al., *Int. J. Pept. Protein Res.* 21:209 (1983)). Although it is possible to determine the entire amino acid sequence of NDS receptor, it is preferable to determine the sequence of peptide fragments of the molecule. If the peptides are greater than 10 amino acids long, the sequence information is generally sufficient to permit one to clone the gene for NDS receptor.

Once one or more suitable peptide fragments have been sequenced, the DNA sequences capable of encoding them are examined. Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977) pp. 356–357). The peptide fragments are analyzed to identify sequences of amino acids that may be encoded by oligonucleotides having the lowest degree of degeneracy. This is preferably accomplished by identifying sequences that contain amino acids that are encoded by only a single codon. Although occasionally such amino acid sequences may be encoded by only a single oligonucleotide, frequently the amino acid sequence can be encoded by any of a set of similar oligonucleotides. Importantly, whereas all of the members of the set contain oligonucleotides that are capable of encoding the peptide fragment and, thus, potentially contain the same nucleotide sequence as the gene that encodes the peptide fragment, only one member of the set contains a nucleotide sequence that is identical to the nucleotide sequence of this gene. Because this member is present within the set, and is capable of hybridizing to DNA even in the presence of the other members of the set, it is possible to employ the unfractionated set of oligonucleotides in the same manner one would employ a single oligonucleotide to clone the gene that encodes the peptide.

In a manner analogous to that described above, one may employ an oligonucleotide (or set of oligonucleotides) having a nucleotide sequence complementary to the oligonucleotide sequence or set of sequences that is capable of encoding the peptide fragment.

A suitable oligonucleotide, or set of oligonucleotides, that is capable of encoding a fragment of the NDS receptor gene (or that is complementary to such an oligonucleotide, or set of oligonucleotides) is identified (using the above-described procedure), synthesized, and hybridized, by means well known in the art, against a DNA or, more preferably, a cDNA preparation derived from human cells capable of expressing NDS receptor gene sequences. Techniques of nucleic acid hybridization are disclosed by Maniatis, T. et al., In: *Molecular Cloning, a Laboratory Manual,* Coldspring Harbor, N.Y. (1987), and by Hayroes, B. D. et al., In: *Nucleic Acid Hybridization,* a Practical Approach, IRL Press, Washington, D.C. (1985), which references are herein incorporated by reference. The source of DNA or cDNA used will preferably have been enriched for NDS receptor sequences. Such enrichment can most easily be obtained from cDNA obtained by extracting RNA from cells cultured under conditions that induce NDS receptor synthesis.

Techniques such as, or similar to, those described above have successfully enabled cloning of genes for human aldehyde dehydrogenases (Hsu, L. C. et al., *Proc. Natl. Acad. Sci. USA.* 82:3771 (1985)), fibronectin (Suzuki, S. et al., *Eur. Mol. Bio. Organ. J.* 4:2519 (1985)), the human estrogen receptor gene (Walter, P. et al., *Proc. Natl. Acad. Sci. USA* 82:7889 (1985)), tissue-type plasminogen activator (Pennica, D. et al., *Nature* 301:214 (1983)) and human term placental alkaline phosphatase complementary DNA (Karo, W. et al., *Proc. Natl. Acad. Sci. USA* 82:8715 (1985)).

In a preferred alternative way of cloning the NDS receptor gene, a library of expression vectors is prepared by cloning DNA or, more preferably, cDNA, from a cell capable of expressing NDS receptor into an expression vector. The library is then screened for members capable of expressing a protein that binds to anti-NDS receptor antibody, and that has a nucleotide sequence capable of encoding polypeptides having the same amino acid sequence as NDS receptor or fragments of NDS receptor.

The cloned NDS receptor gene, obtained through the methods described above, may be operably linked to an expression vector, and introduced into bacterial, or eukaryotic cells to produce NDS receptor. Techniques for such manipulations are disclosed by Maniatis, T. et al., supra, and are well known in the art.

Therapeutic Administration

The preclinical and clinical therapeutic use of the present invention in the treatment of acute inflammatory diseases or disorders of the intestine will be best accomplished by those of skill, employing accepted principles of diagnosis and treatment. Such principles are known in the art, and are set forth, for example, in Petersdorf, R. G. et al., eds., *Harrison's Principles of Internal Medicine,* 10th Edition, McGraw-Hill, publisher, New York, N.Y. (1983).

The molecules, antibodies, and compositions of the present invention, or their functional derivatives, are well suited for the preparation of pharmaceutical compositions. The pharmaceutical compositions of the invention may be administered to any animal that may experience the beneficial effects of the compounds of the invention. Foremost among such animals are humans, although the invention is not intended to be so limited.

The pharmaceutical compositions may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment and the nature of the effect desired.

In addition to the pharmacologically active compounds, the new pharmaceutical preparations may contain suitable pharmaceutically acceptable carriers comprising excipients and auxiliaries that facilitate processing of the active compounds into preparations that can be used pharmaceutically. Preferably, the preparations, particularly those preparations that can be administered orally and that can be used for the preferred type of administration, such as tablets, dragees, and capsules, and also preparations that can be administered rectally, such as suppositories, as well as suitable solutions for administration by injection or orally, contain from about 0.001 to about 99 percent, preferably from about 0.001 to about 95 percent of active compound(s), together with the excipient.

The dose ranges for the administration of the compositions of the present invention are those large enough to produce the desired effect, whereby, for example, the acute inflammation is reduced or eliminated or ameliorated. The doses should not be so large as to cause adverse side effects, such as unwanted cross reactions, anaphylactic reactions, and the like. Generally, the dosage will vary with the age, condition, sex, and extent of the disease in the patient. Counterindications, if any, immune tolerance, and other variables will also affect the proper dosage. The molecules can be administered parenterally by injection or by gradual profusion over time.

The pharmaceutical preparations are manufactured in a manner that is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethyl-cellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings that, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethylcellulose phthalate, are used. Dye stuffs or pigments may be added to the tablets or dragee coatings, for example, for identification or in order to characterize combinations of active compound doses.

Other pharmaceutical preparations that can be used orally include pushfit capsules made of gelatin, as well as soft, sealed capsules made of gelatin and a plasticizer, such as glycerol or sorbitol. The push-fit capsules can contain the active compounds in the form of granules that may be mixed with fillers, such as lactose, binders, such as starches, and/or lubricants, such as talc or magnesium stearate, and, optionally, stabilizers. In soft capsules, the active compounds are preferably dissolved or suspended in suitable liquids, such as fatty oils or liquid paraffin. In addition, stabilizers may be added.

Possible pharmaceutical preparations that can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules that consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension including, for example, sodium carboxymethyl cellulose, sorbitol, and/or dextran. Optionally, the suspension may also contain stabilizers.

Additional pharmaceutical methods may be employed to control the duration of action. Controlled release preparations may be achieved by the use of polymers to complex or adsorb the NDS agents. The controlled delivery may be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release. Another possible method to control the duration of action by controlled release preparations is to incorporate the derivatives of NDS into particles of a polymeric material such as polyesters, polyamino acids, hydrogels, poly(lactic acid) or ethylene vinylacetate copolymers. Alternatively, instead of incorporating the NDS derivatives into these polymeric particles, it is possible to entrap these derivatives in microcapsules prepared, for example, by coacervation techniques or by interfacial polymerization, for example, hydroxymethylcellulose or gelatin-microcapsules and poly(methylmethacrylate) microcapsules, respectively, or in colloidal drug delivery systems, for example, liposomes, albumin microspheres, microemulsions, nanoparticles, and nanocapsules or in macroemulsions. Such teachings are disclosed in *Remington's Pharmaceutical Sciences* (1980).

EXAMPLE I

Neutrophil-Derived Secretagogue

Confluent monolayers of the human intestinal epithelial cell line T84, were grown on collagen-coated permeable supports and maintained until steady state resistance to passive transepithelial ion flow was achieved as previously described (Madara et al., *J. Cell Biol.* 101:2124–2133 (1985); Nash et al., *J. Clin. Invest.* 80:1104–1113 (1987); Nash et al., *Lab Invest.* 59:531–537 (1988)). Such monolayers are composed of cells uniformly adjoined to their neighbors by circumferential tight junctions that dramatically restrict the passive paracellular flow of ions and solutes (Madara et al., *J. Cell Biol.* 101:2124–2133 (1985); Nash et al., *J. Clin. Invest.* 80:1104–1113 (1987); Nash et al., *Lab Invest.* 59:531–537 (1988)). These monolayers serve as models for studies of electrogenic Cl⁻ secretion (Dharmsathaphorn et al., *Am. J. Physiol.* 246:G204–G208 (1984); Dharmsathaphorn et al., *Methods in Enzymology* 192:354–389 (1990)). Transepithelial measurement of resistance to passive ion flow and of short-circuit current were performed as previously described (Madara et al., *J. Cell Biol.* 101:2124–2133 (1985); Nash et al., *J. Clin. Invest.* 80:1104–1113 (1987); Nash et al., *Lab Invest.* 59:531–537 (1988)). In initial experiments, in which PMN's were layered onto T84 monolayers, a modified Ussing-type chamber, which allowed horizontal positioning of monolayers, was used as previously described (Nash et al., *Lab Invest.* 59:531–537 (1988)). For analyses of soluble neutrophil products on epithelial function, both vertically (Madara et al., *J. Cell Biol.* 101:2124–2133 (1985); Nash et al., *J. Clin. Invest.* 80:1104–1113 (1987)) and horizontally mounted monolayers were studied. For the majority of these latter experiments, monolayers prepared as above but having a surface area of 0.33 cm², an apical bath of 0.2 ml, and a serosal bath of 0.8 ml were utilized. This was necessary to circumvent an otherwise prohibitive need for purified PMN's. The reproducibility of electrical data obtained from this system and the similarity of electrical data obtained from these monolayers to that of 2 cm² monolayers was verified.

PMN's were purified from whole blood collected by venipuncture from normal donors of both sexes using a density sedimentation technique previously described (Nash et al., *J. Clin. Invest.* 80:1104–1113 (1987)). The PMN collection procedure was approved by the Brigham and Women's Hospital Human Subjects Committee (protocol 87-1465). PMN's (95% pure) with 98% viability by dye exclusion were suspended in tissue culture medium or in Hanks Balanced Salt Solution at 4° C., and were used for experiments within 1 hour after isolation. $H_2O_2$ was measured as $H_2O_2$ production at 25 minutes in a microtiter assay, as described by Pick and coworkers (Pick et al., *J. Immunol. Meth.* 38:161–170 (1980); Pick et al., *J. Immunol. Meth.* 46:211–226 (1981)).

In subsets of experiments, supernatants from stimulated PMN's were precipitated with two parts ethanol at 4° C. for 30 min. and centrifuged at 9,000–10,000 g for 9–20 minutes. After removing the supernate, the resulting precipitates were resuspended to the initial volume from which they were obtained in Hank's Balanced Salt Solution. Resuspended precipitates were loaded onto solid phase extraction cartridges (C18 SEPPAKS (SEPPAKS is a solid phase matrix which binds molecules to be subsequently eluted off by a series of solvents), Millipore Corp., Milford, Mass.) and the stationary phase was sequentially eluted with hexane, methyl formate, and methanol as described by Serhan and Sheppard (Serhan et al., *J. Clin. Invest.* 85:772–780 (1990)).

All tissue culture reagents were obtained from GIBCO. Bumetanide was obtained from Hoffmann LaRoche, superoxide dismutase and catalase from Worthington Biochemicals, TIMP from Synergen, Boulder, Colo. and all other reagents from Sigma, St. Louis, Mo.

Results

Approximately 400 monolayers were used in these studies.

PMN Activation Elicits Isc Response from T84 Cells

Stimulation of PMN, as determined by $H_2O_2$ production, was achieved with 0.1 µg/ml of PMA in Hanks Balanced Salt Solution (63.3±5.7 nmol $H_2O_2/10^6$ PMN, n=24). In subsets of experiments in which 1 mg/ml bovine serum albumin was present, 1 µg/ml PMA was needed to achieve the same result due to protein sequestration of PMA. However, the presence or absence of protein did not influence the results to be presented below. PMN primed by endotoxin (LPS, 0.1–1 µg/ml, 30–45 min) and subsequently exposed to ForMLF ($10^{-6}$M) produced $H_2O_2$ of 6.8 nmol/$10^6$ PMN (n=16). The above concentrations of LPS, ForMLF, and PMA were used for subsequent experiments.

Figure 1:
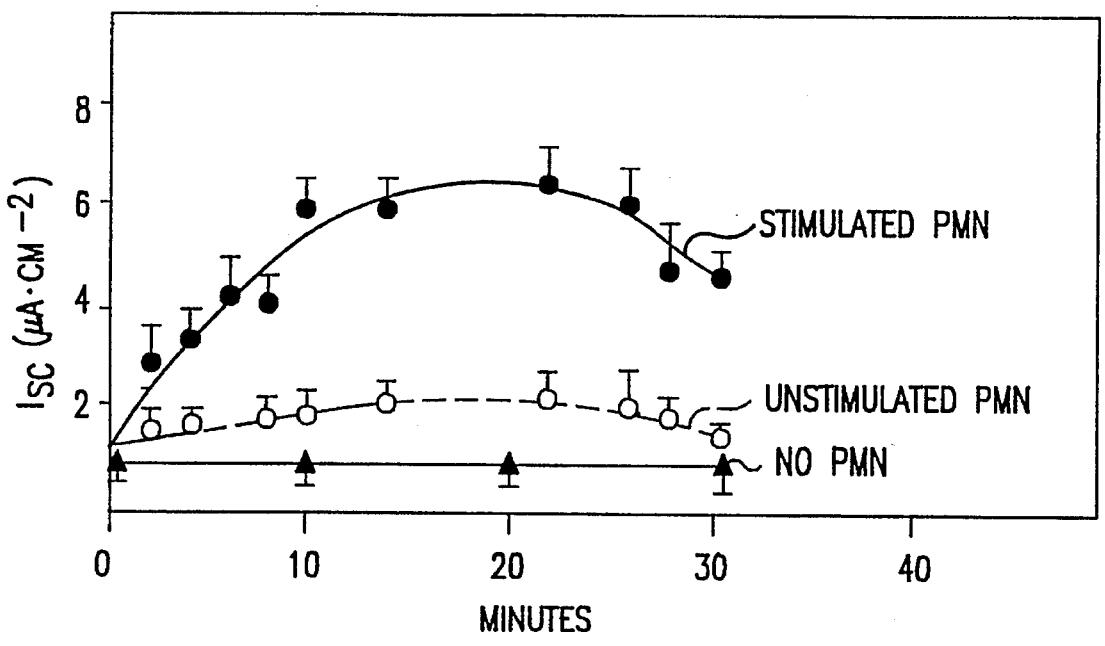
FIG. 1 shows the Isc response of T84 monolayers without PMN's, or with stimulated or unstimulated PMN's layered on the apical surface ($5 \times 10^6$ PMN-$cm^{-2}$). Stimulated PMN's elicited an Isc response detectable within 2 minutes. Although the agonist used here was PMA, comparable results were obtained with LPS-ForMLF. Such agonists, when applied to T84 cells in the absence of PMN, had no significant effect on Isc. (all n=7–12)

LPS-ForMLF or PMA in the doses used to activate PMN had no substantial effect on monolayer resistance or peak short-circuit-current (resistance, 860±24, 795±38, 825±22 ohm·cm²; Isc, 0.6±0.2, 1.9±0.4 0.7±0.4 µAmp cm⁻² for control, PMA exposed, or LPS-ForMLF exposed monolayers, respectively, all n=6–10). Similarly, layering unstimulated PMN on T84 cells (5×10⁶ PMN cm⁻²) had minimal effect on monolayer Isc (FIG. 1), and on monolayer resistance (812±42 vs. 780±30 Ωcm² for monolayers without vs. monolayers with PMN at 20 min). In contrast, LPS-ForMLF or PMA stimulation of PMN in the luminal compartment elicited an Isc that peaked at 10–20 minutes after stimulation, but was detectable within 2 minutes. In the subgroup of experiments from which time course data were initially collected (FIG. 1), the average peak Isc response was ~6 μAmp cm$^{-2}$. The peak response in a large sample of experiments performed in this fashion (PMN first layered onto monolayers, n=52) was 10.5±0.2 μAmp cm$^{-2}$. The extended data, which also include experiments utilizing either PMN or PMN-derived supernatants (to follow below), showed that the peak Isc response varies from ~4–50 μAmp cm$^{-2}$ (n~250). The Isc response did not vary with the method of PMN stimulation (PMA vs. LPS-ForMLF).

Figure 2:
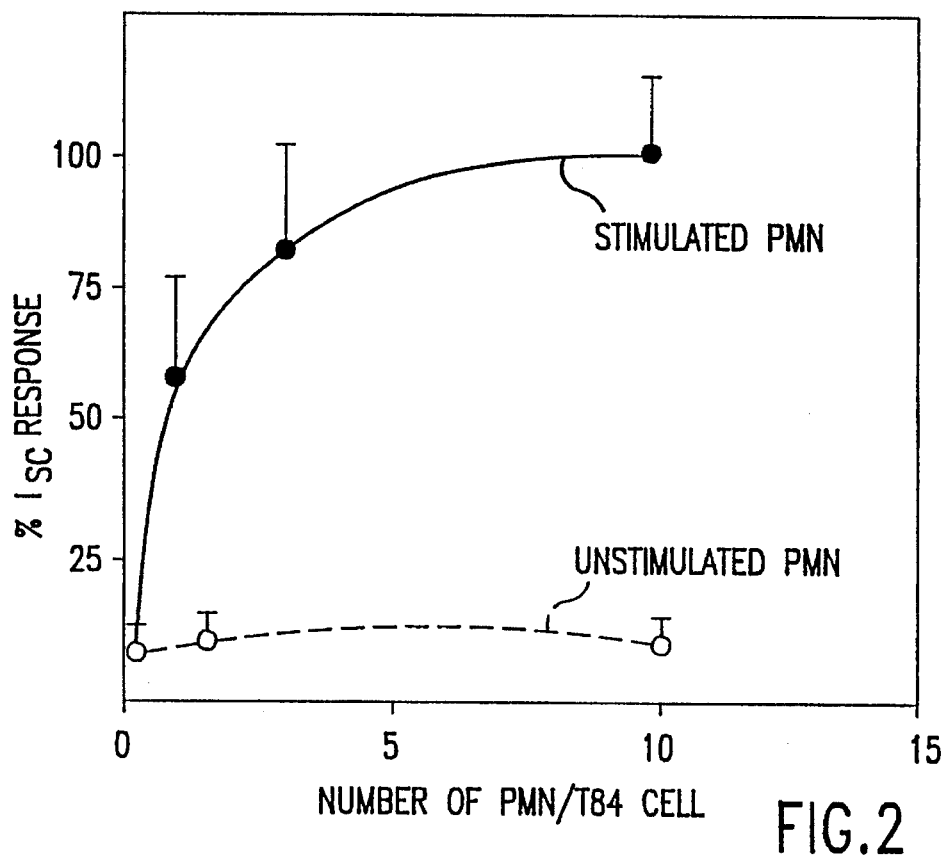
FIG. 2 shows the Isc response elicited by stimulation of PMN as a function of varying PMN:T84 cell ratio. The Isc response can be detected at a PMN:T84 cell ratio of 1:1. PMN:epithelial cell ratios in crypt abscesses in human disease were counted and were found to fall within the range of ratios displayed in the figure. (all n=4–9)

To elicit the above described Isc, stimulated PMN did not need to be present in great excess to T84 cells. As shown in FIG. 2, >50% of the maximal Isc response occurred when stimulated PMN's were present at equal numbers to T84 cells. A greater Isc response (84±16%) was elicited by PMN:T84 cell ratios of 3:1. In these experiments, a PMN:T84 cell ratio of 10:1 was defined as the maximal response both because a PMN:T84 ratio of 20:1 does not elicit a greater response and, as will be shown in the preliminary characterization studies described below, a 3× concentrate of the NDS obtained at the 10:1 density also does not further increase the Isc response. In contrast, both the PMN vehicle (buffer+activator) and unstimulated PMN had little effect on Isc (FIG. 2).

The PMN-elicited Isc Response Does Not Require PMN-T84 Cell Contact

Contact between PMN and T84 cells was not required for the Isc response elicited by PMN activation. PMN separated from T84 cells by an interposed nucleopore filter still elicited an Isc response when stimulated, as did PMN from a patient in leukocyte adhesion deficiency (Arnout, A., *Immun. Rev.* 114:6–36 (1990)). Furthermore, when PMN's were activated in the absence of T84 cells, removed by centrifugation, and the PMN-free supernate placed on T84 monolayers, the Isc response was again obtained (8.7±1.9 vs. 0.4±0.3 μAMP cm$^{-2}$ for supernatant vs. control, P<0.01). These data indicate that PMN-T84 cell contact is not necessary for the Isc response and a soluble mediator is involved in this response.

Figure 3:
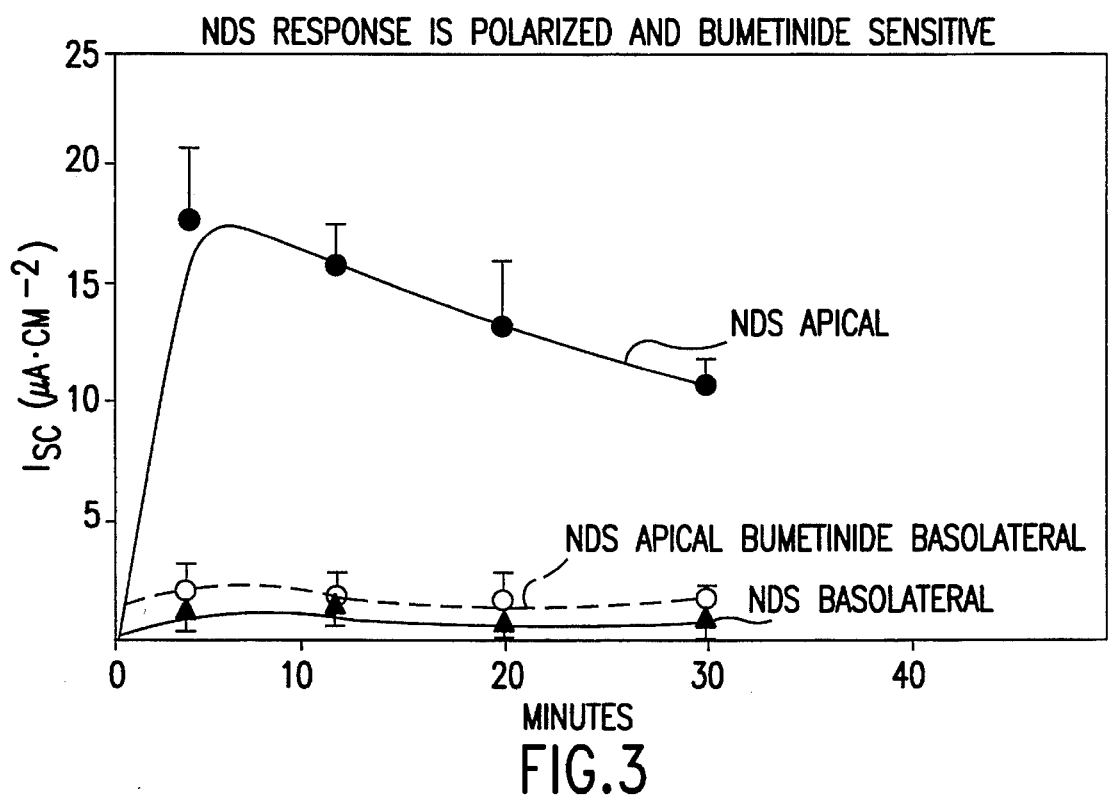
FIG. 3 shows Isc responses to cell-free supernates obtained from stimulated PMN. The neutrophil-derived secretagogue (NDS) activity in the PMN supernate is not active when added to the basolateral side of the monolayers. Bumetinide ($10^{-4}$M, serosal) inhibits 90% of the NDS response. (all n=6–10).

Neutrophil-Derived Secretagogue (NDS) Acts Apically and is Inhibited by Bumetanide As shown in FIG. 3, no NDS activity, as assayed by the Isc response, was detected when NDS was applied basolaterally. Also (FIG. 3) by pre-incubating monolayers with serosal bumetanide, (10$^{-4}$M) for 20–30', the Isc response to apically applied NDS was largely (>85%) inhibited (P<0.01) indicating that the Isc response obtained was due to Cl$^-$ secretion (Dharmsathaphorn et al., *Methods in Enzymology* 192:354–389 (1990)).

NDS is Not H$_2$O$_2$ (Although H$_2$O$_2$ Elicits Isc in T84 Monolayers)

Figure 4:
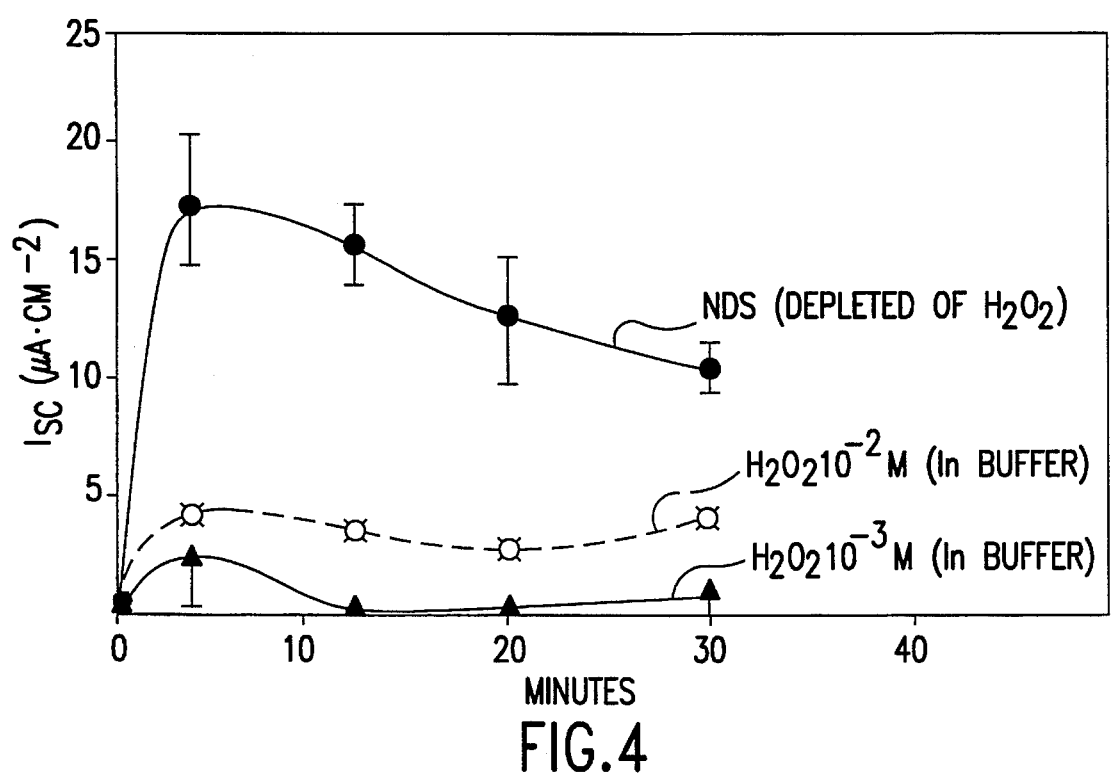
FIG. 4 shows Isc response to $H_2O_2$ or NDS depleted of $H_2O_2$. $H_2O_2$ will elicit a small Isc response when added to the mucosal bath at $10^{-2}$M. Lower concentrations of $H_2O_2$ (including $10^{-4}$M, not shown) have no substantial effect on Isc. However, NDS when depleted of $H_2O_2$ elicits its usual Isc response. NDS activity was also unaffected when PMN supernates were generated in the presence of SOD and catalase. Thus, while it is possible that $H_2O_2$ at high concentration may elicit a very small Isc response directly, NDS activity is not due to $H_2O_2$. (all n=6–9)

Because Powell and coworkers, using mammalian intestinal mucosa, have shown that H$_2$O$_2$ is a Cl$^-$ secretagogue (Karayalcin et al., *J. Clin. Invest.* 86:60–68 (1990)), it was necessary to determine whether NDS represented H$_2$O$_2$. As shown in FIG. 4, H$_2$O$_2$ can also elicit an Isc in T84 monolayers. However, no sustained Isc response is noted with 1 mM H$_2$O$_2$ (or with 0.1 mM) and with 10 mM H$_2$O$_2$ the maximum response is far less than the NDS response obtained in parallel experiments (4.4±0.5 vs. 17.5±2.9 μAmp cm$^{-2}$ for 10 mM H$_2$O$_2$ vs. NDS, respectively, P<0.01). The NDS containing supernate used in this experiment was incubated at 20° C. for 1 hr before the experiment, conditions that led to a loss of H$_2$O$_2$ (H$_2$O$_2$ of this NDS supernate <10$^{-4}$M). In agreement with these findings, as shown in Table I, NDS activity was also not ablated when the supernatant was generated in the presence of superoxide dismutase and catalase.

Also examined were the effects of other inhibitors of neutrophil products or metabolic pathways on the ability of PMN to generate NDS activity when stimulated. As shown in Table I, none of the inhibitors tested significantly attenuated NDS activity (PMN's were preincubated with all inhibitors before stimulation). Pretreatment of PMN with cytochalasin B (5 μg/ml) for 30 minutes before stimulation with PMA also did not enhance NDS activity. These latter conditions potentiate PMN degranulation upon subsequent stimulation by soluble agonists (Zurier et al., *Proc. Natl. Acad. Sci. USA* 70:844–848 (1973)) and thus such data suggest NDS is not a product contained in PMN granules. Lastly, as shown in Table I, the failure of protease inhibitors to ablate NDS activity in supernates of stimulated PMN suggests that NDS activity is likely not due to proteolysis of another PMN product or the effects of PMN-derived proteases on the apical membrane of T84 cells. In agreement with this latter point, NDS is smaller than PMN-derived proteases (see below).

TABLE I

| Inhibitors of PMN metabolic pathways do not diminish Isc response to NDS | | |
|---|---|---|
| Inhibitor | Product Effected | % Loss of NDS Activity |
| Sodium azide, 1 mM (n = 17) | Myeloperoxidase Products (i.e. hypochlorite monochloramine) | 0% (NS) |
| Catalase, 5000 U/ml (n = 4) | H$_2$O$_2$ | 10 ± 7% (NS) |
| Catalase$^+$ SOD, 5000 U/ml + 280 U/ml (n = 11) | Reactive oxygen species | 0% (NS) |
| DFP, 5 mM (n = 6) | Serine Proteases (i.e. elastase, cathepsin G, proteinase 3) | 29 ± 14% (NS) |

TABLE I-continued

Inhibitors of PMN metabolic pathways do not diminish Isc response to NDS

| Inhibitor | Product Effected | % Loss of NDS Activity |
| --- | --- | --- |
| Heparin, 10 μg/ml (n = 5) | Heparinase | 25 ± 9% (NS) |
| TIMP, 20 μg/ml (n = 8) | Metaloproteinases | 24 ± 7% (NS) |
| Mepacrine, 150 μM (n = 7) | Phospholipase A2 (cyclooxygenase, lipogenase products) | 0% (NS) |
| Esculatine, 100 μM (n = 5) | Lipooxygenases (12LO > 5LO) | 0% (NS) |

Preliminary Analyses of Physical Characteristics of NDS

NDS activity was not ablated by either 1 μM trypsin or 1 μM chymotrypsin for 2 hr at 37° C. (83±12 and 87±9% of control value); was not lost after 40 min boiling (96±10% of control value); was not sensitive to 0.1% trifluoroacetic acid (70% of control value); and withstood lyophilization and resuspension (92% vs. control value). In four experiments, 41–70% of NDS activity, as defined by the Isc response, could be recovered from ethanol precipitates of the PMN supernate. However, unlike NDS activity in a PMN supernate, the NDS activity of the resuspended pellet was largely lost at a 3× dilution—indicating that only a small amount of the compound(s) responsible for NDS activity were precipitated out. NDS activity also does not appear to be associated with a highly hydrophobic compound(s) such as a phospholipid, leukotriene, prostaglandin, or peptidolipid; NDS activity could not be extracted by hexane, methyl formate, or methanol (2 experiments, each with n=3–6 for each solvent; all solvent extracts contained <8% of NDS activity). Lastly, 94±8% (n=12) of NDS activity passed through an ultrafiltration device with a 500 nominal molecular weight cut off, indicating the NDS activity resides within a pool of rather small compound(s).

Discussion

PMN's stimulated by PMA or LPS-ForMLF, release a soluble small, heat and acid stable, hydrophilic, and trypsin-resistant compound that acts apically on T84 cells to elicit a bumetinide-sensitive Isc, indicative of $Cl^-$ secretion. Although $H_2O_2$ can elicit $Cl^-$ secretion when applied to intestinal mucosa (Karayalcin et al., *J. Clin. Invest.* 86:60–68 (1990)), the Isc response generated by $H_2O_2$ in T84 cells is less than that of NDS. Also, NDS activity is not sensitive to catalase, and supernates from activated PMN that have been depleted of $H_2O_2$ have full NDS activity. Recently, monochloramine, a myeloperoxidase product of PMN, has been shown to elicit $Cl^-$ secretion in T84 monolayers (Tamai et al., *Gastroenterology* 98:A557 (1990)). However, in contrast to this small compound, NDS is active only when applied to the luminal side of T84 cells. Furthermore, NDS activity is not attenuated when myeloperoxidase activity of PMN is inhibited before PMN activation. Adenosine, another potential PMN product, also stimulates $Cl^-$ secretion but, in contrast to NDS, does so efficiently whether applied apically or basolaterally (Barrett et al., *Am. J. Physiol.* 256:C197–C203 (1989)). Additionally, NDS activity is unattenuated if PMN's are treated with a lipoxygenase inhibitor before stimulation, and extraction of NDS containing precipitates with solvents known to isolate lipoxygenase products (Serhan et al., *J. Clin. Invest.* 85:772–780 (1990)) does not isolate any NDS activity. Lastly, because LPS-ForMLF-stimulated PMN generated NDS activity as efficiently as PMA stimulated PMN, the NDS-stimulated Isc cannot be attributed to a PMN derived factor active only if T84 cells are "primed" with phorbol ester.

Of interest is that the neutrophil:epithelial cell ratios used in this example are well within the range of those actually found in crypt abscesses (Nash et al., *J. Clin. Invest.* 80:1104–1113 (1987)) and that the conditions for PMN activation by LPS-ForMLF exist within the colonic lumen (van Deventer et al., *Gastroenterology* 94:825–831 (1988); Chadwick et al., *Scand. J. Gastro.* 23:121–128 (1988)). The foregoing results in T84 cells suggest that PMN stimulated in intestinal crypt abscess may release a secretagogue(s) active only from the apical membrane of the cell. The only other known $Cl^-$ secretagogue that is effective from the apical, but not the basolateral, pole of intestinal epithelia or T84 cells is a compound far larger than NDS, heat stable toxin of *E. coli* (Huott et al., *J. Clin. Invest.* 82:514–523 (1988)). NDS may contribute to diarrheal disease seen in states of acute intestinal inflammation.

EXAMPLE II

Microassay System and Its Use to Assess the Cytoskeletal Response During $Cl^-$ Secretion The human intestinal epithelial cell line, T84, was utilized to prepare confluent monolayers on glass or on permeable collagen-coated supports as previously described (Hecht et al., *J. Clin. Invest.* 82:1516–1524 (1988)). Monolayers were allowed to grow to steady-state resistance values (Madara et al., *J. Cell Biol.* 101:2124–2133 (1985)). In some experiments collagen-coated permeable supports had a surface area of 2 $cm^2$ (Madara et al., *J. Cell Biol.* 101:2124–2133 (1985)); however, to circumvent the otherwise prohibitive costs of NBD-phallicidin, collagen-coated permeable supports of 0.33 $cm^2$ were used for several experiments. The monolayer morphology, the response to secretagogues, and the effect of NBD-phallicidin preloading on the responses measured, did not vary between these two monolayer sizes. Transepithelial solute fluxes and measurements of resistance and short circuit current (Isc), a measure of $Cl^-$ secretion in T84 cells, were obtained as previously described (Dharmsathaphorn, et al., *Am. J. Physiol.* 246:G204–G208 (1984); Dharmsathaphorn, et al., *J. Clin Invest.* 75:462–471 (1985); Hecht, et al., *J. Clin. Invest.* 82:1516–1524 (1988)).

Protein synthesis, as measured by leucine incorporation, was performed according to the methods of Critchlow et al.

and Kastyo et al. (Critchlow et al., *Gastroenterology* 88:237–249 (1985); and Kostyo et al., *Endocrinology* 65:395–401 (1959)). Lactic dehydrogenase (LDH) release was measured as before (Hecht et al., *J. Clin. Invest.* 82:1516–1524 (1988)). For fluorescence studies, monolayers were fixed and labeled with rhodamine-phalloidin as previously described in detail (Hecht et al., *J. Clin. Invest.* 82:1516–1524 (1988)). F-actin content was measured by the method of Howard and Oresajo (Howard et al., *J. Cell Biol.* 101:1078–1085 (1985)).

NBD-phallicidin and rhodamine-phalloidin were obtained from Molecular Probes Inc. (Junction City, Oreg.), dried under pure nitrogen gas and reconstituted in media or buffer (i.e., without vehicle). Nystatin was used from a stock solution of 5 mg/ml in methanol and was obtained from Sigma (St. Louis, Mo.). Radioisotopes were obtained from New England Nuclear (Boston, Mass.) and all other reagents were obtained from Sigma (St. Louis, Mo.). Statistical analysis was performed by paired Student's t test or ANOVA as specified.

Results

Electrical Response to cAMP/Analysis of Paracellular Pathway

Figure 5:
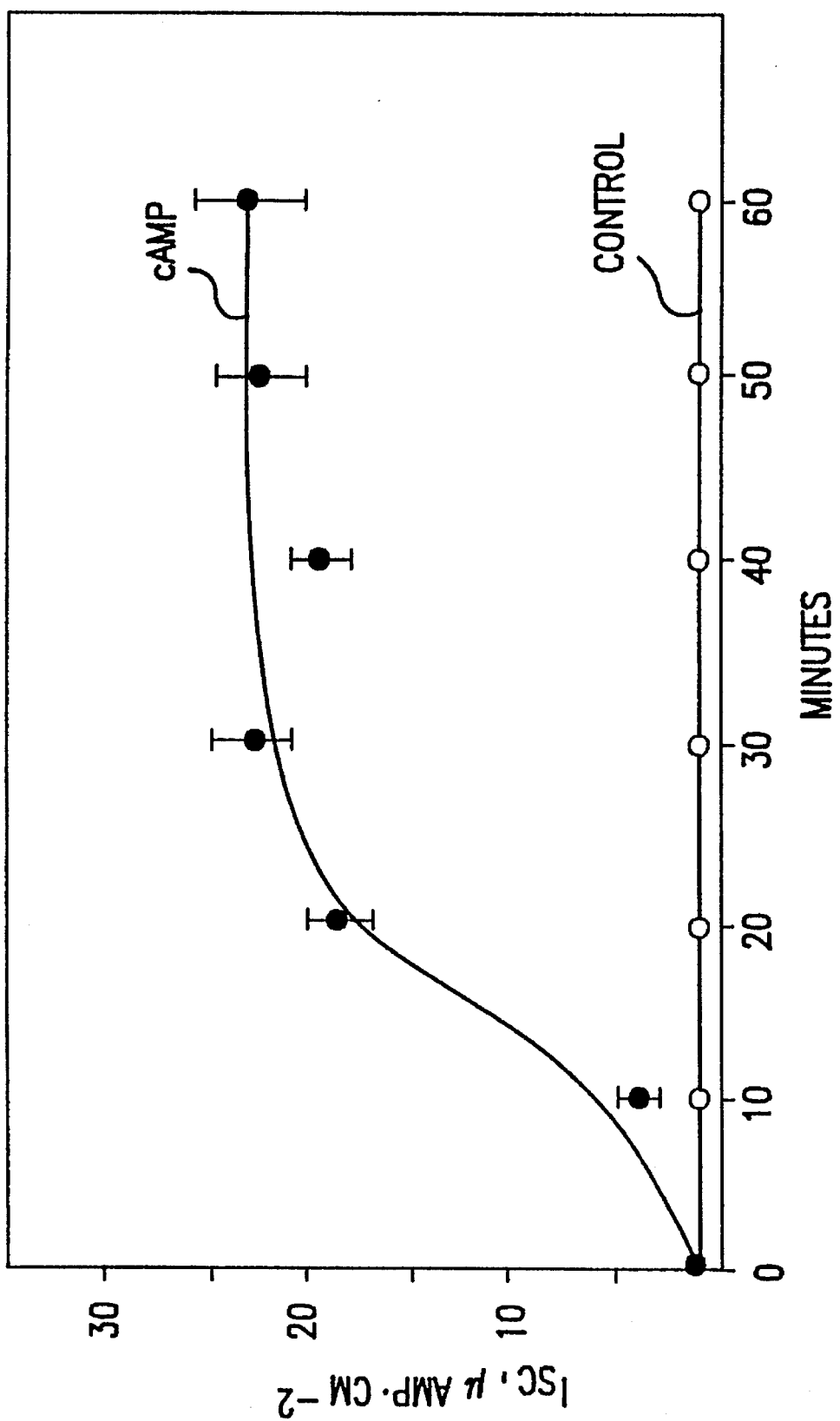
FIG. 5 shows Isc response to 1 mM 8-bromo-cAMP in T84 cells. Isc, a measure of Cl$^-$ secretion in T84 monolayers (Dharmsathaphorn et al., *J. Clin. Invest.* 75:462–471 (1985)), peaks after 30 minutes and persists over the ensuing 30 minutes. Isc is of relatively small magnitude in the control group (vehicle only). (n for each point=6–12; cAMP and control groups significantly different P<0.01 by ANOVA, F value=58.7).
Figure 6A:
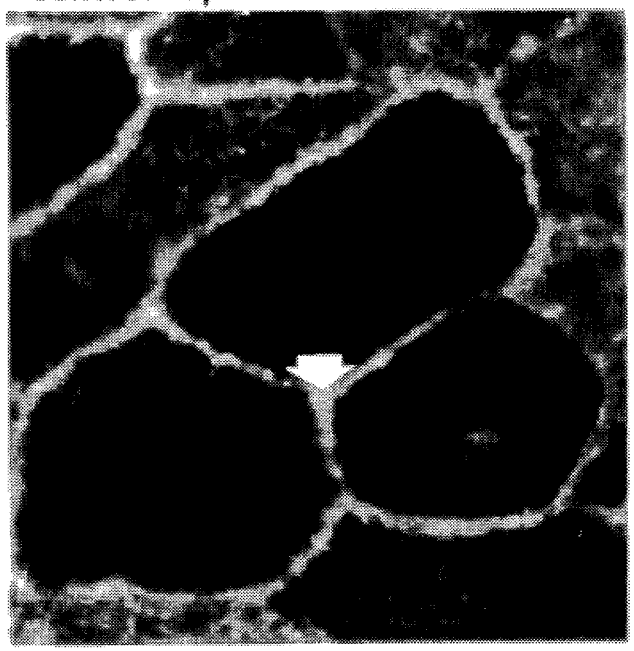
FIGS. 6A–D show fluorescent localization of F-actin T84 monolayers, viewed enface, in control monolayers (top) (FIGS. 6A–6B) and in monolayers exposed for 30–60 minutes to 1 mM 8-bromo-cAMP and 1 mM theophylline (bottom). Different optical planes of focus are obtained using Nomarski optics. In the left panels, (FIGS. 6A and 6C) the plane of focus is at the apical membrane and the perijunctional ring of actin (arrowheads) is seen. The fine flocculated actin centrally in the cell at this level represents microvillus-associated F-actin as well as F-actin underlying the apical membrane. The distribution of F-actin in the apical pole of the cell is not discernably affected by cAMP. In the right panels (FIGS. 6B and 6D), the optical plane of focus is at the basal pole of T84 cells. Here the fine, randomly dispersed pattern of F-actin in composing the basolateral cytoskeletal cortex of controls (top right) (FIG. 6B) is replaced by thickened bundles (arrowheads) of peripherally relocated F-actin with central clearing (asterisk) after cAMP exposure (bottom right) (FIG. 6D). Such changes in F-actin in the basal aspect of T84 cells were observed to occur within 30 minutes of exposure with 1 mM 8-bromo-cAMP and 1 mM theophylline. (X~1800)
Figure 6B:
Figure 6C:
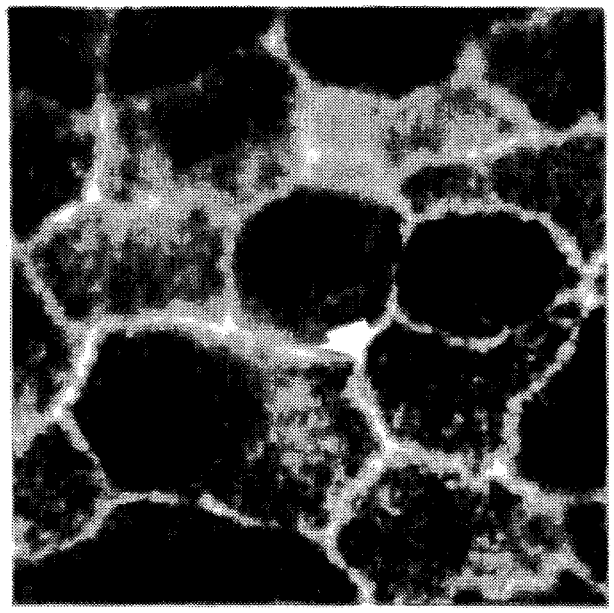
Figure 6D:
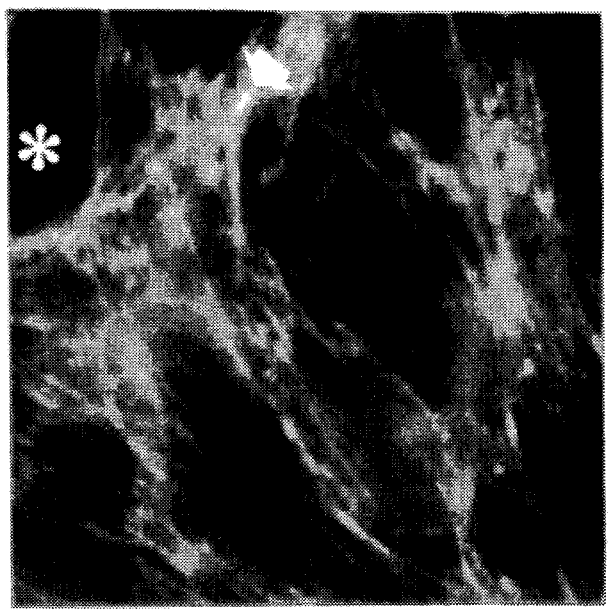

As shown in FIG. 5, elevation of intracellular cAMP elicits an increase in Isc that has been shown by others to represent a $Cl^-$ secretory current (Dharmsathaphorn et al., *J. Clin. Invest.* 75:462–471 (1985); Weymer et al., *J. Clin. Invest.* 76:1828–1836 (1985); and Cartwright et al., *J. Clin. Invest.* 76:1837–1842 (1985)). After addition of 1 mM 8-bromo-cAMP (the standard condition of cAMP stimulation unless otherwise noted), Isc rose to peak at $22.5 \pm 1.9$ $\mu A/cm^2$ by 30 minutes. This secretory response was subsequently maintained over the next thirty minutes (FIG. 5). In parallel to the increase in Isc, resistance decreased ($63 \pm 3$ vs. $91 \pm 1\%$ of baseline value for cAMP exposed vs controls respectively at 30 minutes, $P<0.05$). Since it has been previously shown that resistance across T84 monolayers can be modulated by alterations in tight junction permeability, putatively due to alterations in the perijunctional actin-myosin ring (Madara et al, *J. Membr. Biol.* 100:149–164 (1987); Madara et al., *J. Cell Biol.* 102:2125–2136 (1986); and Madara et al., *J. Cell Biol.* 102:2125–2136 (1986)), and since cAMP has been shown to alter paracellular permeability characteristics in other epithelia (Duffy et al., *Nature* 294:451–453 (1981); Jacobson, H. R. *Am. J. Physiol.* 236:F71–F79 (1979); and Stelzner et al., *J. Cell Physiol.* 139:157–166 (1989)), it was initially questioned whether the observed resistance changes were due to cytoskeletally mediated changes in tight junctions. This hypothesis that was, in fact, the original basis for initiating the experiments reported here was subsequently proven false: first, transepithelial mannitol fluxes did not increase after cAMP ($104\pm8\%$, $106\pm5\%$, $149\pm14\%$, vs. $113\pm10\%$, $116\pm7\%$, $136\pm11\%$, for three consecutive 20 minute flux periods for control and cAMP stimulated monolayers respectively, P=NS, total n=15); second, and similarly, serosal to mucosal $^{22}Na$ flux was not enhanced following cAMP ($107\pm9$, $108\pm5\%$, $128\pm10\%$ vs. $112\pm7\%$, $108\pm8\%$, $128\pm11\%$ for three consecutive 20 minute flux periods relative to baseline monolayer for control and cAMP, respectively, P=NS, total n=19); and last, as will be detailed, and in contrast to other states in which T84 cell tight junction permeability is altered (Hecht et al., *J. Clin. Invest.* 82:1516–1524 (1988); Madara et al., *J. Cell Biol.* 102:2125–2136 (1986)), no changes in F-actin distribution in the area of the perijunctional actin-myosin ring were identified following cAMP exposure. These findings are consistent with the hypothesis that the resistance decrease seen after cAMP exposure is due to a transcellular $Cl^-$ current, not to a change in the paracellular pathway.

Effects of cAMP on F-actin Distribution and Content

As shown in FIG. 6, cAMP induced regionally restricted and profound alterations in F-actin distribution in T84 cells. These changes were readily apparent 30 min. after stimulation and were maintained over the following 30 minute period in parallel to the cAMP-induced Isc response shown in FIG. 5. As shown in the left-hand panels of FIG. 6, which are taken in the plane of the apical perijunctional actin-myosin ring, cAMP did not elicit an alteration in perijunctional ring F-actin, a finding that is in agreement with the lack of effect of cAMP on junctional permeability. In contrast, as shown on the right-hand panel, which shows optical sections of F-actin distribution in the basal pole of the cell, cAMP alters the distribution and appearance of basolateral F-actin microfilaments. In control monolayers, F-actin in the basal pole of the cell consists of a finely dispersed array of homogenous microfilaments. After cAMP exposure, F-actin at this basal site is displaced to the cell periphery as thickened bundles that surround the cleared central zone. In a blinded review of randomly obtained photomicrographs (59 from cAMP and 60 from control), it was possible to use the above differences in basolateral F-actin distribution to correctly identify the treatment group in 87% of micrographs. In two subsequent groups of experiments graded for the presence of thickened, peripherally marginated basolateral F-actin, blinded analyses of randomly obtained photomicrographs showed: 72% and 93%, respectively, of photographs of cAMP-stimulated monolayers have these changes as opposed to 11% and 20% of controls (data for 30 and 60 minute experiments, respectively, total of 186 micrographs and 23 monolayers were used in these analyses). It also appeared that the evolution of the cAMP-elicited cytoskeletal change paralleled the change in Isc: 38% of images were judged to contain the above changes at a time when the Isc response was half maximal (n=52; half maximal effort at 15 min, $\mu Amp\ cm^{-2}$ under unstirred conditions).

Next to be determined was whether the basolateral redistribution of F-actin elicited by cAMP was accompanied by a net change in cellular F-actin content (e.g., net depolymerization). F-actin content was determined in 8 monolayers stimulated with cAMP (1 mM 8-bromo-cAMP, 1 mM theophylline) and compared to that in 7 control monolayers. Although the specific F-actin binding of cAMP monolayers was only 76% of controls, this comparison did not show a significant difference from control values ($39\pm3$ vs. $53\pm8$ units$\times 10^{-3}/\mu g$ protein for cAMP and control respectively, P=0.09).

Stabilization of F-actin Cytoskeleton by NBD-Phallicidin Preloading

Figure 7:
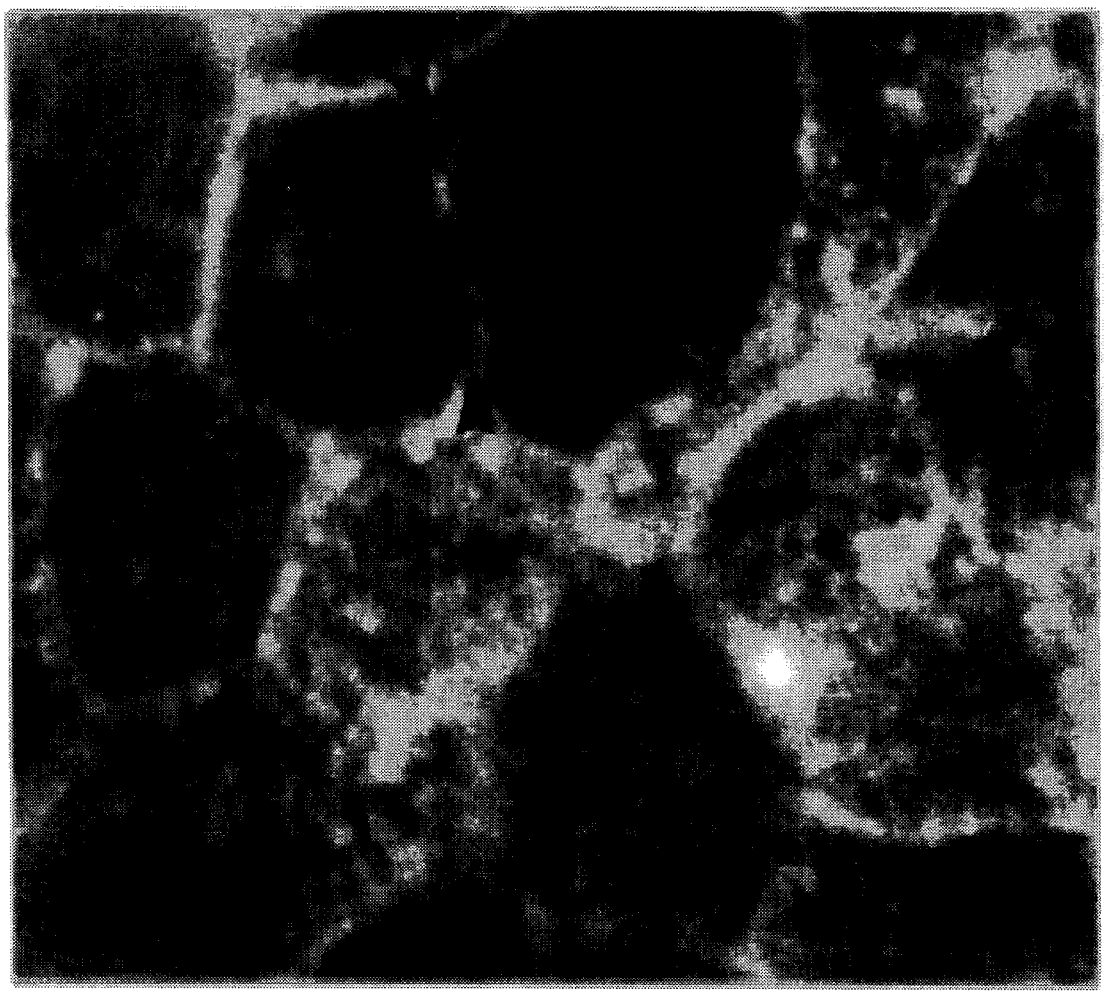
FIG. 7 shows an en face photomicrograph of F-actin distribution within a T84 monolayer seen after coincubation with 1 μM NBD-phallicidin. NBD, a weak and readily quenched fluorophore, allows fluorescent visualization of the distribution of the loaded phallicidin. As would be expected for the distribution of F-actin, in the apical pole of the cell, perijunctional rings are identified (arrowhead). Thus, simple coincubation of T84 cells with NBD-phallicidin permits entry of this probe into the cytosolic space where it binds F-actin.

Several approaches were utilized to load cells with NBD-phallicidin. The transient permeabilization procedure used by Barak and colleagues (Barak et al., *Proc. Natl. Acad. Sci. USA* 77:980–984 (1980)) in mesenchymal cells was found not to be applicable since it was associated with a marked reduction in transepithelial resistance. By modifying techniques employed in nonepithelial cells, it was found that simple coincubation of epithelial monolayers with this reagent eventually led to its internalization as had been described for loading nonepithelial cells with nontoxic concentrations of nitrobenzoxadiazole (NBD)-phallicidin (Barak et al., *J. Cell Biol.* 89:368–372 (1981)). Monolayers were coincubated for 1–5 hours in media containing NBD-phallicidin concentrations ranging from 0.1–10 µM. This simple coincubation permitted NBD-phallicidin uptake and association with cytoskeletal F-actin as shown in FIG. 7. Since the NBD-phallicidin concentration was low, it was not surprising that the labelling of the cytoskeleton seen after loading was weak and readily quenched during observation. It was also noted that monolayers could be loaded with no discernible toxicity by incubating them for 1.5 to 5 hours with 0.5 µm NBD-phallicidin. As shown in Table II, NBD-phallicidin loading did not increase LDH release or diminish [$^3$H]leucine incorporation into protein. Significantly, transepithelial resistance, a general electrical parameter that also serves as an extremely sensitive indicator of toxicity, was also unaffected by NBD-phallicidin loading (Table II). Lastly, as shown in the table, loaded cells were able to actively pump $Na^+$ as judged by their steady-state Isc response to the apically added $Na^+$ ionophore nystatin (500 U/ml). In separate experiments it was determined that the concentration of vehicle used (methanol) did not independently affect monolayer resistance or secretory response. It should be noted that all the data in the table were collected from monolayers loaded for 3–6 hours although, as detailed below, a shorter loading period may be sufficient to negate the cAMP-elicited cytoskeletal (and $Cl^-$ secretory) response.

TABLE II

Effects of NBD-Phallicidin Loading on T84 Monolayers

Figure 8C:
FIGS. 8A–C show enface photomicrographs of F-actin localization in the basal pole of T84 cells in control monolayers (left) (FIG. 8A), monolayers exposed to 1 mM 8-bromo-cAMP and 1 mM theophylline for 60 minutes (center) (FIG. 8B) and in monolayers preloaded with NBD-phallicidin and subsequently stimulated with cAMP as above for 60 minutes (right) (FIG. 8C). Here the F-actin distribution is highlighted with a rhodamine probe at the end of the experiment to intensify the signal. As can be seen, NBD-phallicidin pre-loading largely prevents the cAMP-elicited F-actin reordering.
Figure 8B:
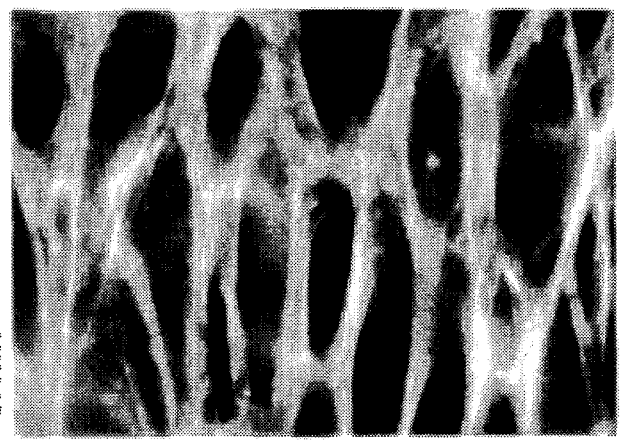
Figure 8A:

|  | Loaded | Control | P |
|---|---|---|---|
| LDH release (% of total content) | 15 (pool of 5) | 12 (pool of 4) |  |
| [$^3$H]leucine incorporation (DPM/µg protein) | 75 ± 8 (n = 7) | 87 ± 6 (n = 7) | NS |
| Resistance (ohm-cm$^2$) | 350 ± 24 (n = 23) | 301 ± 20 (n = 22) | NS |
| Steady State Isc | 2.5 ± 0.4 | 3.2 ± 0.4 |  |
| Response to Nystatin (µA/cm$^2$) | (n = 12) | (n = 10) | NS | cAMP Exposure Fails to Remodel F-actin or Stimulate $Cl^-$ Secretion in T84 Monolayers Preloaded with NBD-Phallicidin As shown in FIG. 8, the dramatic cAMP-elicited rearrangement of F-actin in the basal portion of T84 cells is attenuated by pre-loading cells with NBD-phallicidin. This inhibitory effect was semi-quantitatively assessed in one group of experiments: photographs were obtained from areas of control and cAM P exposed monolayers (which demonstrated F-actin patterns described previously) and compared to photographs taken from unselected areas of cAMP-exposed but NBD-phallicidin preloaded monolayers. Four monolayers from each group were examined. Blinded review of this sample of NBD-phallicidin preloaded and cAMP exposed monolayers yielded images that were judged to be indistinguishable from controls in 44% of micrographs. The remaining 56% of micrographs in this group were identified as exhibiting partial but subtle cAMP-like changes separable from the full cAMP response although not indistinguishable from the "normal" pattern. Thus, NBD-phallicidin preloading profoundly inhibited the cAMP-elicited cytoskeletal response.

Figure 9:
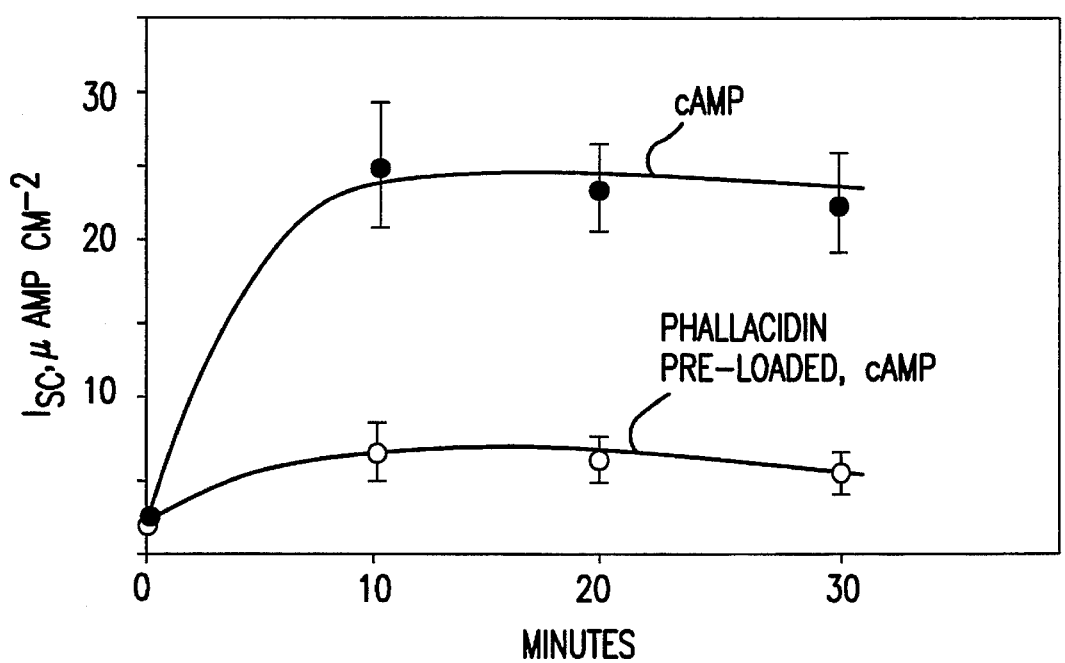
FIG. 9 shows the time course of Isc response to cAMP in control monolayers (top curve) and in monolayers preloaded with NBD-phallicidin (bottom curve). In contrast to controls, monolayers preloaded with NBD-phallicidin have a markedly attenuated Isc response to cAMP (P<0.01, ANOVA, F=24.15). Since controls unexposed to cAMP display Isc of 1–3 μAMP (not shown), NBD-phallicidin substantially inhibits the cAMP response. (n=6 and 7 for control and NBD-phallicidin preloaded curves, respectively.) Loading conditions may affect the degree of inhibition of the cAMP response.
Figure 10:
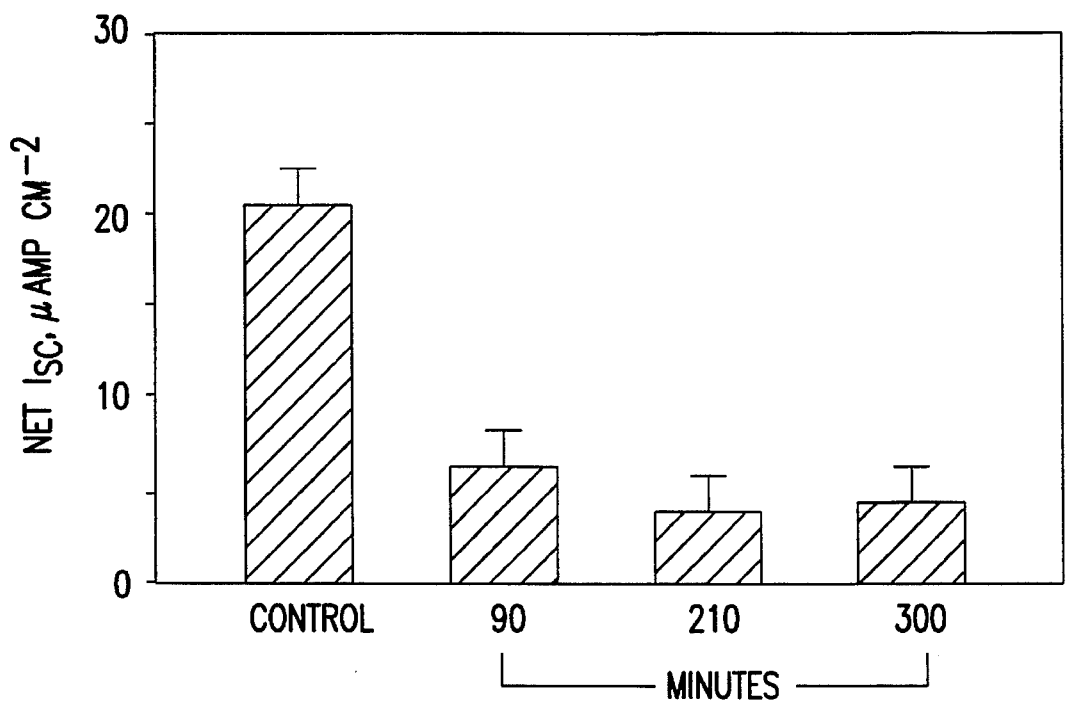
FIG. 10 shows the net Isc response to 30 minute stimulation with cAMP in low passage number (<60) T84 cells preloaded with 0.5 μM NBD-phallicidin for various periods of time. Net Isc in control monolayers (20.7±2.2 μA/cm$^2$, n=12) produced by 30 minute exposure to cAMP (left column) is significantly greater than the response in Isc achieved in monolayers preloaded NBD-phallicidin for 90 minutes (6.75±0.7 μA/cm$^2$, n=4), for 210 minutes (4.4±0.7 μA/cm$^2$, n=5), or for 300 minutes (4.7±0.7, n=11) (P>0.05, P<0.01, ANOVA, F=23.65). The inhibition seen with 90 minutes loading is not significantly less than with the longer periods for these low passage number cells. Higher passage cells need longer loading periods to achieve substantial inhibition of cAMP-elicited Cl$^-$ secretion.

As shown in FIGS. 9 and 10, NBD-phallicidin preloaded monolayers also had markedly attenuated Isc responses to cAMP. In initial experiments utilizing cells of low passage number (<60), it was noted that NBD-phallicidin preloading for as short as 90 min. was sufficient for inhibiting the cAMP-elicited rearrange of F-actin (and the $Cl^-$ secretory response). Higher passage number cells may require longer loading periods for NBD-phallicidin loading presumably due to passage-related alterations in plasma membrane permeation by this reagent. As indicated in Table 2 and further supported by the carbachol data (see below), even several hours of incubation with NBD-phallicidin does not impair the functional viability of monolayers.

NBD-phallicidin loading also inhibits cAMP-elicited $Cl^-$ secretion at cAMP concentrations below that at which maximal secretion can occur. At 0.2 mM 8-bromo-cAMP, a dose that elicits 14.5% of the maximal Isc response, NBD-phallicidin preloading still exerts substantial inhibitory effects on Isc (77.3% inhibition as compared with controls, n=5; 5.28±0.9 vs. 22.7±2.8 µA cm$^{-2}$ at 12 min for NBD-phallicidin loaded vs. control monolayers.

Figure 11:
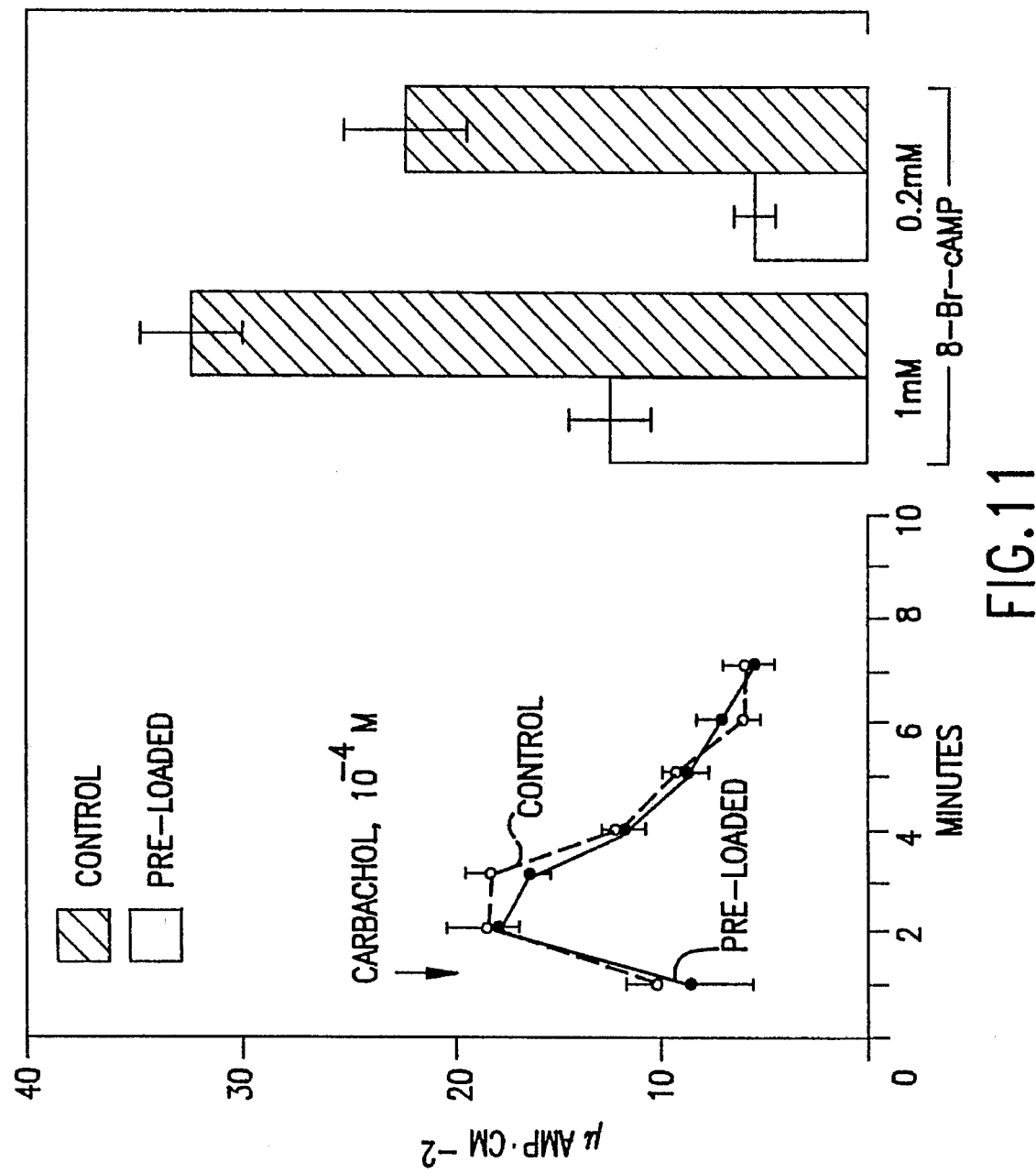
FIG. 11 shows that NBD-phallicidin preloading attenuates cAMP but not carbachol-elicited Isc. Carbachol ($10^{-4}$M) elicits a short-lived Cl$^-$ secretory response (not paralleled by a rearrangement of F-actin) that is unaffected by NBD-phallicidin preloading. In contrast, paired experiments show the usual inhibition of 1 mM 8-Br-cAMP-elicited Cl$^-$ secretion by preloading. Furthermore, separate experiments using lower doses of cAMP (0.2 mM) that elicit Cl$^-$ secretory responses of similar magnitude to those elicited by $10^{-4}$M carbachol, also show substantial inhibition of C$^-$ secretion. n=7 for each carbachol curve. n=5–7 for each cAMP bar. Monolayers were loaded by coincubation with NBD-phallicidin for about 16 hr for these experiments.

Carbachol Stimulated $Cl^-$ Secretion Is Not Attenuated by NBD-phallicidin Loading To see whether NBD-phallicidin loading also attenuated $Ca^{++}$-induced $Cl^-$ secretion, the effects of loading on carbachol-elicited Isc were assessed (Dharmsathaphorn et al., *J. Clin. Invest.* 77:348–354 (1986)). As shown in FIG. 11, loading conditions (here 12–16 hr) that greatly attenuated the Isc response to 8-bromo-cAMP did not effect the Isc response to carbachol. Since the carbachol-elicited Isc is not influenced by NBD-phallicidin preloading, it was of interest to see whether F-actin re-arrangement parallels the rapid Isc response elicited by carbachol. F-actin distribution at the peak of the carbachol-elicited Isc response did not appear qualitatively different from that in control monolayers. This impression was confirmed by semi-qualitative analyses similar to those outlined above that showed no significant expression of the pattern elicited by cAMP with carbachol (11% vs. 9% for control vs. carbachol, respectively, n=35 images for each).

Discussion

This example shows that cAMP elicits a redistribution of F-actin in T84 cells and that inhibition of the cAMP-elicited cytoskeletal response also substantially inhibits the cAMP-elicited $Cl^-$ secretory response. Inhibition of these cAMP-elicited cytoskeletal and $Cl^-$ secretory responses occurs under conditions in which T84 cells are able to carry out normal synthetic functions, 10 able to form barriers to passive ion flow, able to pump $Na^+$ in response to a $Na^+$ ionophore, and able to secrete $Cl^-$ in response to carbachol, hence demonstrating retention of several cellular functions, including general electrophysiological parameters and the specific ability to secrete $Cl^-$.

This example also defines a simple method by which the F-actin cytoskeleton can be stabilized in an epithelium without exerting detectable toxicity and without disrupting the monolayer. This method, which likely will be adaptable to other epithelia, provides a means of assessing the contribution of F-actin to transport events in confluent monolayers. The interaction of phallicidin with the cytoskeleton is well characterized (Cooper, J. A., *J. Cell Biol.* 105:1473–1478 (1987)). Phallicidin binds avidly to F-actin ($K_d < 0.1$ μM) and prevents depolymerization of actin oligomers (Barak et al., *J. Cell Biol.* 89:368–372 (1981); Cooper, J. A., *J. Cell Biol.* 105:1473–1478 (1987)). These facts make phallicidin, and the native compound phalloidin, extremely useful F-actin specific probes. In fact, in this example, these compounds have been used in two ways other than to load cells: as a fluorescent probe for F-actin localization and as a biochemical probe to quantitate F-actin content of cells, both widely accepted as well as characterized methods (Hecht et al., *J. Clin. Invest.* 82:1516–1524 (1988); Howard et al., *J. Cell Biol.* 101:1078–1085 (1985)). It was originally assumed that plasma membranes were impermanent to phallicidin and thus initial studies utilizing this reagent in living cells, as has been done here, relied on microinjection (Hamaguchi et al., *Cell Motility* 2:103–113 (1982)) or transient reversible permeabilization (Barak et al., *Proc. Natl. Acad. Sci. USA* 77:980–984 (1980)). More recently, however, it has been noted that NBD-conjugated phallicidin can be loaded into nonepithelial cells by simple coincubation (Barak et al., *J. Cell Biol.* 89:368–372 (1981); Phillips et al., *Am. J. Physiol.* 257:C562–C567 (1989)). Whether by microinjection, permeabilization, or incubation loading, conditions could be identified in endothelial cells, fibroblasts, and chick embryo cells that allowed F-actin labelling without cytotoxicity (Barak et al., *Proc. Natl. Acad. Sci. USA* 77:980–984 (1980); Barak et al., *J. Cell Biol.* 89:368–372 (1981); Cooper, J. A., *J. Cell Biol.* 105:1473–1478 (1987); and Phillips et al., *Am. J. Physiol.* 257:C562–C567 (1989)). As shown by Phillips et al., loading of endothelial cells with non-toxic doses of NBD-phallicidin prevents the thrombin-induced increases in endothelial permeability that appear to occur due to thrombin-induced cytoskeletal contraction (Phillips et al., *Am. J. Physiol.* 257:C562–C567 (1989)). The use of this reagent may provide initial insights into the poorly studied but important area of cytoskeletal influences on ion transport in epithelia.

In summary, a cAMP-elicited change in F-actin that parallels the $Cl^-$ secretory response to this mediator in T84 cells is described. NBD-phallicidin loading of T84 cells can be performed by a simple coincubation without detectable cellular toxicity. The stabilization of F-actin in T84 cells by this technique inhibits both the change in F-actin and $Cl^-$ secretory response typically elicited by cAMP but does not alter other electrical parameters of monolayer function. Lastly, both the rearrangement of F-actin and the inhibition of the $Cl^-$ secretory response seen in NBD-phallicidin preloaded cells does not occur with $Ca^{++}$-mediated $Cl^-$ secretion induced by carbachol.

EXAMPLE III

Microassay System and its Use to Analyze PMN Transmigration Access Epithelia PMN migration across intestinal crypt epithelium is a structural hallmark of a variety of active intestinal diseases such as ulcerative colitis, Crohns disease, and infectious enterocolitis (Kumar et al., *Am. J. Surg. Path* 6:523–529 (1982); Yardley, J. H., *In Recent developments in the therapy of inflammatory bowel disease,* Myerhoff Center for Digestive Disease at Johns Hopkins, Baltimore, Md. 3–9 (1986)). The degree of PMN transmigration into intestinal crypts and formation of crypt abscesses is an indicator of disease severity (Yardley et al., *The Gastrointestinal Tract,* J. H. Yardley and B. C. Morrison, editors, Williams and Wilkins Co., Baltimore, p. 57 (1977)), yet little is known concerning the mechanisms by which PMN's migrate across epithelia. This transmigratory event has previously been modeled in vitro using isolated peripheral blood human PMN and epithelial monolayers derived from T84 cells (Nash et al., *J. Clin. Invest.* 80:1104–1113 (1987)), a human intestinal epithelial cell line with crypt-like features (Madara et al., *Gastroenterology* 92:1113–1145 (1987); Dharmsathaphorn et al., *Meth. Enzymol.* 5:912:354–389 (1990); and Dharmsathaphorn et al., *Am. J. Physiol.* 246:G204–G208 (1984)). Use of this model showed that PMN's induced to migrate across T84 monolayers do so by impaling intercellular tight junctions (TJ) and, putatively due to the resulting defects in TJ, transepithelial resistance falls and TJ permeabilities to inert paracellular solutes reversibly increase (Nash et al., *J. Clin. Invest.* 80:1104–1113 (1987)). Structural studies of this transmigratory event suggest that epithelial-PMN adhesive event(s) might be required (Nash et al., *Lab. Invest.* 59:531–537 (1988)). Although PMN-epithelial adhesive interactions have, in general, not been well characterized, studies of PMN-endothelial adhesive interactions indicate that several PMN surface ligands may participate in PMN adherence to blood vessel walls. Among the most prominent of these are three heterodimeric PMN surface proteins that share a common subunit ($\beta_2$, CD18) and belong to a superfamily of cell adhesive proteins termed integrins (Ruoslahti, E., *J. Clin. Invest.* 87:1–5 (1991)). It has been found that the CD11b/CD18 (Mol/Mac-1) member of this glycoprotein family is required for PMN-T84 cell adhesive interactions that permit transepithelial migration to proceed. These studies were aided by development (reported in this example) of an extremely simple, highly efficient assay of transmigration that permits large numbers of epithelial monolayers to be studied in parallel. Lastly, this assay has been modified to permit assessment of PMN transmigration in the "serosal-to-mucosal" direction; the direction that occurs naturally in the intestine. Due to technical difficulties, investigators, including the inventor, have in the past largely studied PMN transmigration across epithelia in the mucosal-to-serosal direction. These latter studies reveal that PMN transmigration is markedly more efficient in this "physiological" direction, but that transmigration in this direction also requires a CD11b/CD18 mediated event.

Methods

Cell culture and assay systems

Figure 13:
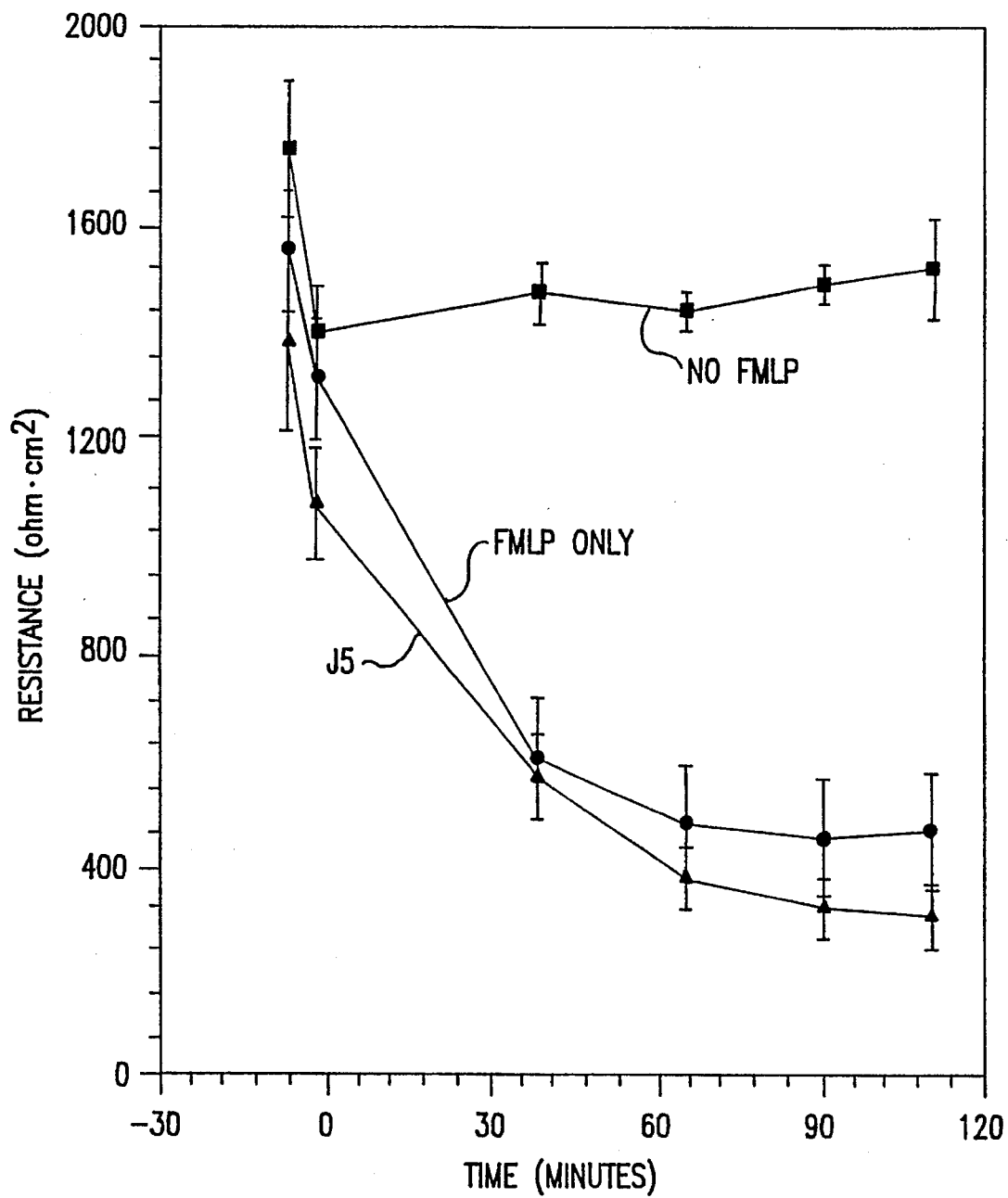
FIG. 13 is a representative experiment showing the effect on transepithelial resistance of ForMLF-elicited PMN transmigration (mucosal-to-serosal) across T84 monolayers. PMN's were added to monolayers at time 0. In the absence of ForMLF, resistance was stable from 0–120 minutes. In contrast, in the presence of ForMLF with or without J5, an antibody that binds to non-CD11/CD18 related PMN surface epitopes at high density (Arnaout, M. A., et al., *J. Clin. Invest.* 72:171–179 (1983); Ritz, J., et al., *Nature* (Lond.) 283:583–585 (1980)), marked decreases in resistances were observed. Resistances were calculated as described in Example III and in Madara et al., *J. Cell Biol.* 101:2124–2133 (1985); Dharmsathaphorn et al., *Methods in Enzymology* 192:354–389 (1990)); and Dharmsathaphorn et al., *American Journal of Physiology* 9:G204–G208 (1984). Each condition is the mean of 5 monolayers±SE. One representative experiment of 5.
Figure 14:
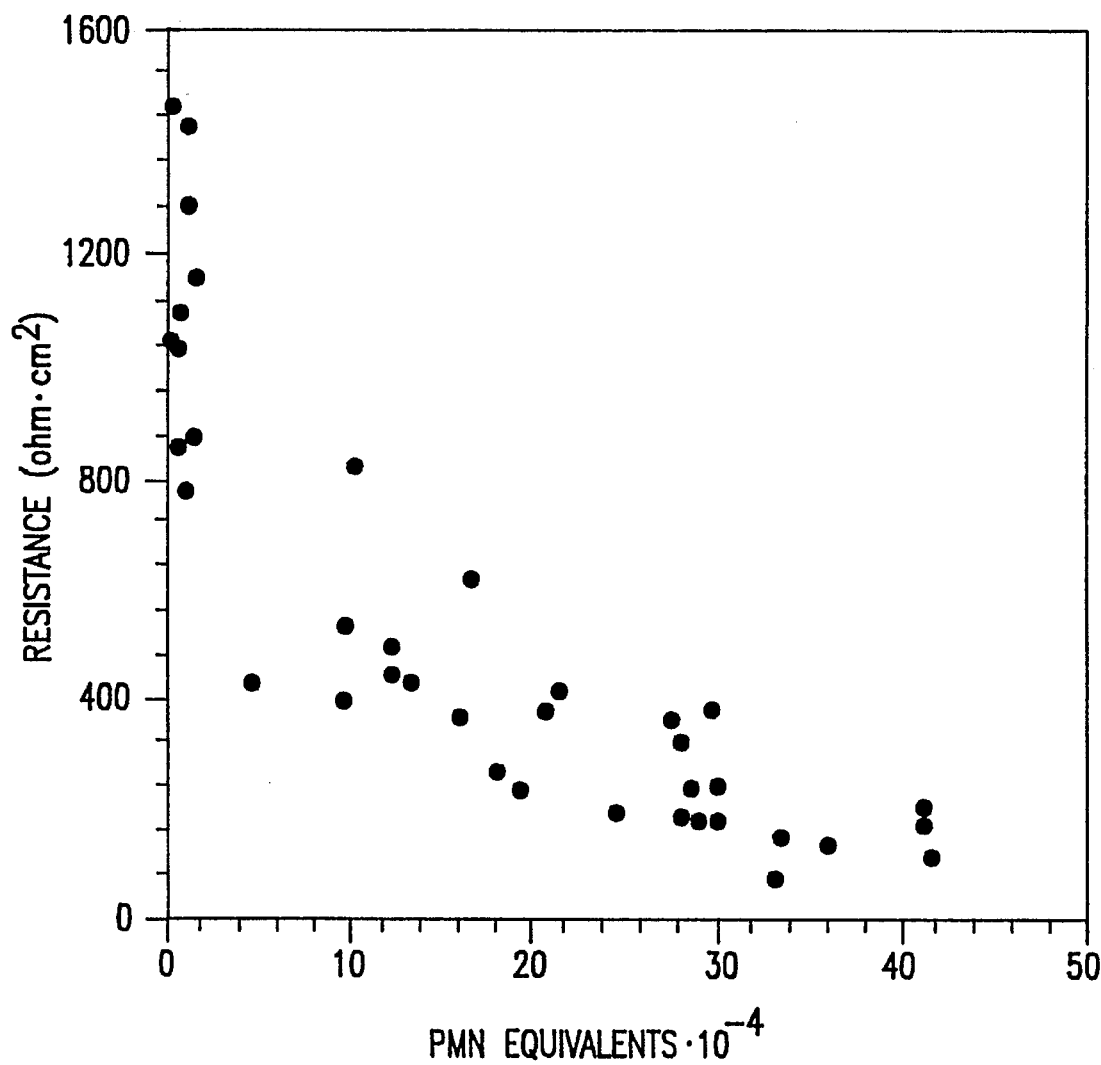
FIG. 14 is a comparison of numbers of transmigrated PMN's as assessed by MPO with effects on transepithelial resistance (variable transmigration densities elicited by using ForMLF gradients ranging from $10^{-6}$–$10^{-7}$M and harvesting monolayers at 100 min.) PMN's on monolayers with no ForMLF gradient were used as controls. When migrating in the mucosal-to-serosal direction, the fall in resistance correlates well with the number of transmigrated PMN's and saturates after migration of >1–2×10⁵ PMN equivalents.

T84 cells (passages 70–100) were grown and passaged as previously described (Madara et al., *J. Cell Biol.* 101:2124–2133 (1985); Dharmsathaphorn et al., *Methods in Enzymology* 192:354–389 (1990); and Dharmsathaphorn et al., *American Journal of Physiology* 9:G204–G208 (1984)). In initial experiments, monolayers grown on 2 $cm^2$ polycarbonate filters that had been coated with ammonia-precipitated, glutaraldehyde-crosslinked collagen were used (Cerijido et al., *J. Cell Biol.* 77:8a53–880 (1978)). In later experiments, to diminish reservoir volume and permit large numbers of parallel experiments to be performed, commercially available ring-supported polycarbonate filters with a surface area of 0.33 $cm^2$ were used (Costar inserts, Costar Corp., Cambridge, Mass.). While T84 cells do not attach well to such filters unless collagen coated, acceptable collagen coating could be accomplished by placing 50 μl of viscous rat-tail collagen solution (Cerijido et al., *J. Cell Biol.* 77:853–880 (1978)) diluted 1:100 with 60% ethanol in each well and allowing them to dry overnight (FIG. 12). Such treatment also substantially diminishes matrix depth and eliminates the matrix precipitation and crosslinking steps that impair the ability of PMN to transmigrate across the matrix. As a result, serosal-to-mucosal PMN transmigration can also be studied by constructing inverted monolayers (FIG. 12 13). To make inverted monolayers (thus permitting gravitational settling of PMN on the serosal aspect of the monolayer), polycarbonate rings of the same diameter as the insert base and 1 mm in height were glued to the bottom of inserts (FIG. 12 B). Inverted filters were treated with rat-tail collagen as above, and T84 cells were plated onto the inverted inserts and allowed to attach overnight after which the inserts were righted into 24-well culture plates, maintained for 6–14 days to achieve electrical stability (Madara et al., *J. Cell Biol.* 101:2:124–2133 (1985)) and then used. Polycarbonate rings were glued to the inserts with RTV Silicone Rubber (General Electric), which has the dual advantage of not releasing trace cytotoxic solvents after setting and of being non-conductive, thus preventing current leaks across the assembly. The volumes used in the upper and lower reservoirs of the inserts were 0.2 and 1.0 ml, respectively.

Electrical assays were performed on 2-$cm^2$ rings as previously described (Madara et al., *Gastroenterology* 92:113–1145 (1987)); Dharmsathaphorn et al., *Meth. Enzymol.* 192:354–389 (1990; Dharmsathaphorn et al., *Am J. Physiol.* 246 (Gastrointest. Liver Physiol. 9):G204–G208 (1984)) but were modified for monolayers grown on inserts. Rather than being mounted in modified Ussing chambers (Madara et al., *Gastroenterology* 92:113–1145 (1987)); Dharmsathaphorn et al., *Meth. Enzymol.* 192:354–389 (1990; Dharmsathaphorn et al., *Am J. Physiol.* 246 (Gastrointest. Liver Physiol. 9):G204–G208 (1984)) or sterile chambers (Hecht et al., *J. Clin. Invest.* 82:1516–1524 (1988)) as previously described, inserts were studied in the 24-well plates in which they were grown. As shown in FIG. 12, the serosal and mucosal reservoirs were each interfaced with calomel and Ag-AgCl electrodes Via 5% agar bridges made with HBSS. Measurements of resistance were obtained using a dual voltage clamp (University of Iowa) as described before (Madara et al., *Gastroenterology* 92:113–1145 (1987); Dharmsathaphorn et al., *Meth. Enzymol.* 192:354–389 (1990); Dharmsathaphorn et al., *Am J. Physiol.* 246 (Gastrointest. Liver Physiol. 9):G204–G208 (1984)) except that current pulses of 25 µA were used since 100 µA currents lead to time-dependent polarization effects that would have necessitated current pulses in the millisecond range for accurate reading. Electrical readings obtained from such inserts were highly reproducible (as will be reflected by the data shown below) and correlated well with data obtained from standard Ussing chambers (as can be seen by comparing the data from FIG. 13 with that from Nash et al., *J. Clin. Invest.* 80:1104–1113 (1987)). The only positional effects noted in this system occur when the tips of the agar bridges in the outer well abut the bottom of the plate, a problem that can be avoided by cutting the ends of these bridges to a 45°–60° taper. For studies reported here, ~700 monolayers were used, the vast majority of which were on 0.33 $cm^2$ inserts.

Transmigration experiments

To ensure constant temperature, all experiments were carried out in a constant 37° C. environment. Insert-monolayer assemblies were lifted from wells, the medium was discarded, and the entire insert was gently washed in HBSS (Sigma, St. Louis, containing, in g/L, $CaCl_2$ 0.185, $MgSo_4$ 0.098, KCl 0.4, $KH_2PO_4$ 0.06, NaCl 8, $Na_2HPO_4$ 0.048, glucose 1, type H1387) to which was added 10 mM HEPES pH 7.42.

Inserts were then placed into new wells containing HBSS and allowed to equilibrate for 5–15 min. To ensure that contaminating serum factors did not influence the observed results, in a subset of experiments monolayers were washed in HBSS two days prior to the experiment and were subsequently maintained in insulin and transferrin-supplemented serum free media until use. PMN, isolated as described previously (Henson et al., *J. Clin. Invest.* 56:1053–1061), were induced to transmigrate utilizing a 1 µM gradient of ForMLF ((Nash et al., *J. Clin. Invest.* 80:1104–1113 (1987)). Where used, antibodies were added to the upper reservoir ("mucosal" for monolayers in unmodified inserts and "serosal" for inverted monolayers—see FIG. 12) 15 minutes before addition of PMN. In apical-to-basolateral transmigration experiments, PMN's were added to a final density of $6 \times 10^6$ $cm^{-2}$ from a 5× PMN stock suspended in HBSS without calcium or magnesium.

Chemotaxis assay

PMN contents of monolayers and lower reservoirs were quantitated by assaying the azurophil granule marker, myeloperoxidase (MPO) as described previously (Parkos et al., *J. Biol. Chem.* 260:6541–6547 (1984)) with slight modifications. Briefly, inserts containing monolayers were washed five times with HBSS to remove non-migrated PMN. Myeloperoxidase was then released by solubilization of monolayers in 1.0 ml of HBSS containing 0.5% Triton X-100. To the lower reservoirs, 50 µl of 10% Triton X-100 in $H_2O$ was added for a final concentration of 0.5%. The pH was then adjusted to 4.2 with 100 µl of 1.0M citrate buffer pH 4.2. For each sample, color development was assayed at 405 nm on a Bio-Rad microtiter plate reader after mixing equal parts of sample and a solution containing 1 mM 2,2'-azino-di-( 3-ethyl) dithiazoline sulfonic acid (ABTS) and 10 mM $H_2O_2$ in 100 mM citrate buffer pH 4.2, 20° C. After appropriate color development the reaction was terminated by the addition of sodium dodecyl sulfate to a final concentration of 0.5%. The assay was standardized with known concentrations of the same PMN used in each experiment and was linear in the range used (0.3–50×$10^4$ cells/ml). MPO activity was negligible in lysates of T84 monolayers unexposed to PMN. The measured MPO contents of reservoirs (or filters) accurately reflected PMN-associated MPO since cell-free (microfuged) supernatants of both reservoirs contained <3% of total MPO activity.

Morphologic studies

Monolayers were fixed in 2% glutaraldehyde in HBSS at the end of representative experiments and processed for 1 µm Epoxy sections as previously described (Madara et al., *J. Cell Biol.* 101:2124–2133 (1985); and Madara et al., *J. Cell Biol.* 101:2124–2133 (1985)).

Data presentation

Since variations may exist both in monolayer resistance between groups of monolayers and in PMN obtained from different donors, individual experiments were performed using large uniform groups of monolayers and PMN from single donors. The figures shown are of representative experiments each of which were repeated as indicated in the legend. Data are presented as means±standard error.

Results

Mucosal-to-serosal transmigration

Inserts: A simple reliable assay system for epithelial transmigration

It has previously been shown that ForMLF induced mucosal-to-serosal transmigration across 2 cm² monolayers subsequently mounted in Ussing-type chambers results in a fall in transepithelial resistance putatively due to reversible disruption of T84 tight junctions (Nash et al., *J. Clin. Invest.* 80:1104–1113 (1987)). The transmigration-associated resistance responses across the 0.33 cm² inserts used for these studies are shown in FIG. 13. In this group of 15 monolayers, the baseline resistance was 1581±80 ohm·cm². After 110 min. of ForMLF-induced transmigration, in the absence of antibody, the resistance fell by 71% to 458±99 ohm·cm². This ForMLF-induced response was not significantly different from that occurring in the presence of a control antibody, J5, where resistance fell by 79% to 295±55 ohm·cm². The time course of the resistance fall in FIG. 13 had a $t_{1/2}$ of 30 minutes with a near maximal response at 90 minutes. With different PMN preparations, the $t_{1/2}$ value varied by only 10 minutes from that shown in FIG. 13. The PMN dose response of transepithelial resistance fall was also similar to that previously reported in 2 cm² monolayers grown on crosslinked collagen and studied in modified Ussing chambers ((Nash et al., *J. Clin. Invest.* 80:1104–1113 (1987)); maximal responses were generally elicited with PMN densities of 3–6×10⁶ cells/cm² with small responses occurring at cell densities <4×10⁵ cells/cm² (maximal fall from baseline resistance at 90 min; 13%).

Serosal-to-Mucosal Transmigration

Since PMN migration across intestinal epithelia in disease states normally occurs in the serosal-to-mucosal direction, the direction opposite to that generally studied in epithelia due to technical considerations, the inventor devised a method for investigating transmigration across "inverted" T84 cell monolayers using a modified version of the simple assay system described above (see FIG. 12 and METHODS).

Serosal-to-Mucosal Transmigration Is Highly Efficient

Figure 15:
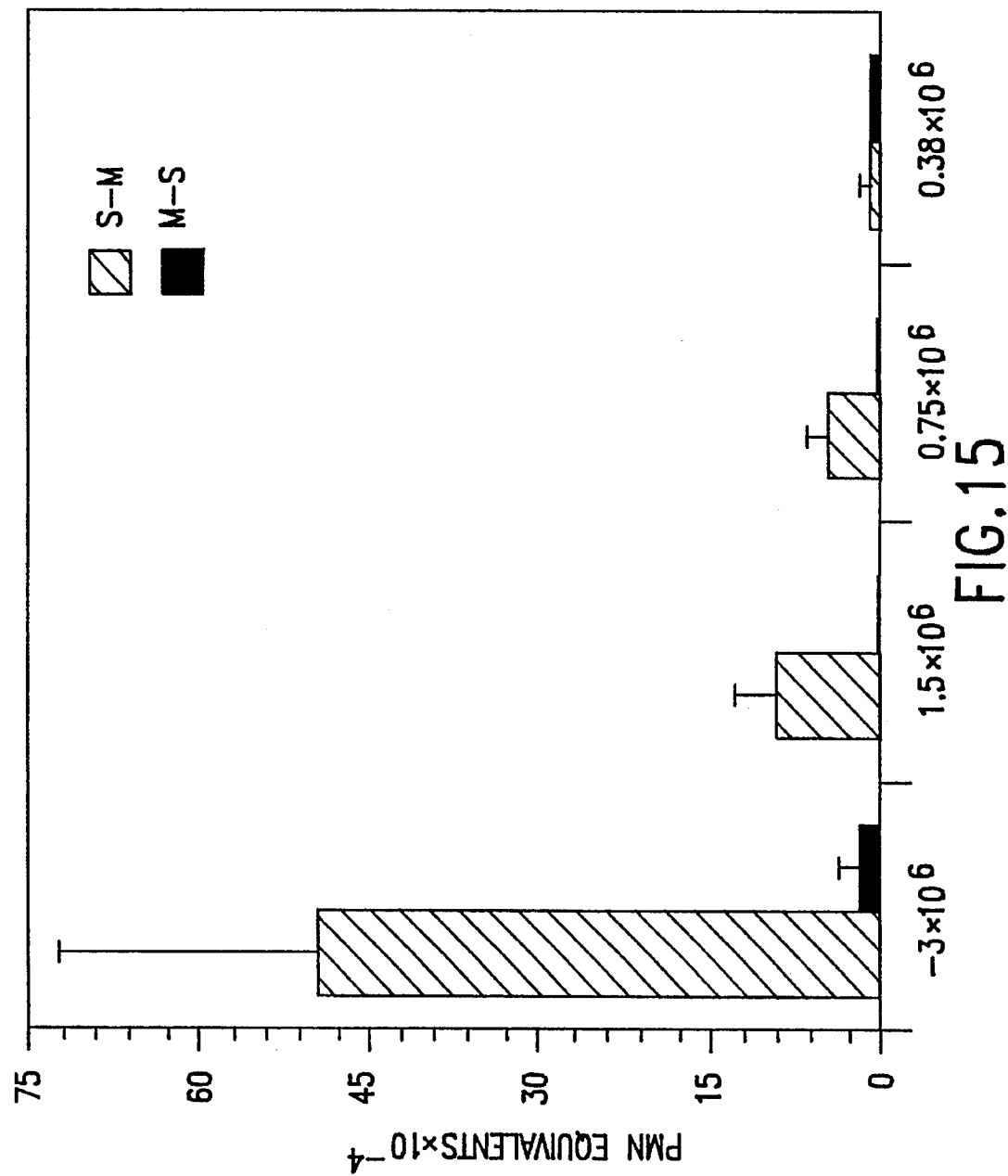
FIG. 15 shows the effect of PMN density on numbers of migrated PMN's in serosal-to-mucosal versus mucosal-to-serosal transmigration experiments. PMN's were layered onto the mucosal or serosal aspect of T84 monolayers at the densities shown (per cm²) and induced to transmigrate for 110 minutes as described in Example III. PMN's appearing in lower reservoirs were quantitated by the MPO assay as described in Example III. S-M refers to serosal-to-mucosal transmigration; M-S refers to mucosal-to-serosal transmigrations. There is a 5–20-fold increase in transmigration in the physiologic, or serosal-to-mucosal direction. Each bar is the mean of three monolayers±SE.

To compare the efficiency of transmigration of PMN across the epithelium in the serosal-to-mucosal vs the mucosal-to-serosal direction, experiments were performed using uniform conditions (passage of epithelia, neutrophil donor, experimental conditions). As shown in FIG. 15, PMN transmigration in the natural serosal-to-mucosal direction was markedly more efficient than that in the opposite direction. For the mucosal-to-serosal experiment, dilution of PMN to a density of 1.5×10⁶ PMN/cm² (¼ the standard density) yielded no measurable PMN equivalents in the lower reservoir after 110 min. In contrast, for the serosal-to-mucosal experiment, the dilution of PMN resulting in no measurable transmigration was 0.38×10⁶ PMN/cm² (¹⁄₁₆ the standard density). Comparison of MPO data from all experiments done in both directions under standard conditions revealed that serosal-to-mucosal transmigration is consistently 5–20 times more efficient than in the opposite direction.

Electrical Assays In Evaluating Serosal-to-Mucosal Transmigration

PMN transmigration in the serosal-to-mucosal direction elicits a large decrease in transepithelial resistance (22±3% of baseline value, at 110 min for positive control). Inhibition of transmigration under reduced PMN densities results in inhibition of the transmigration-associated resistance response although, even at very low PMN densities, the final resistance value in the inhibited state is still substantially less than the baseline value. Under conditions promoting serosal-to-mucosal transmigration, the effect on resistance is also much greater than that encountered in the mucosal-to-serosal direction. Indeed, the epithelium is so sensitive to transmigration in this direction that direct measures of transmigration, such as MPO, are preferable to resistance assays in these experiments.

Discussion

In a variety of organs (lung, kidney, urinary bladder, etc.) including the intestine, neutrophils traverse both the endothelial lining of blood vessels and subsequently the epithelium during acute inflamenation. While the complex events related to PMN transendothelial migration are being widely addressed ((Dana et al., *J. Clin. Invest.* 73:153–159 (1984); Arnaout et al., *J. Cell Physiol.* 137:305–309 (1988); Smith et al., *J. Clin. Invest.* 82:1746–1756 (1988); and Luscinskas et al., *J. Immunol.* 142:2257–2263 (1989)), those related to transepithelial migration have received less attention (Evans et al., *Br. J. Exp. Path.* 64:644–654 (1983); Cramer et al., *J. Cell Biol.* 102:1868–1877 (1986); Parsons et al., *Am. J. Pathol.* 129:302–312 (1987); Migliorisi et al., *J. Leukocyte Biol.* 44:485–492 (1988)). However, such transepithelial migration of PMN is of substantial clinical importance. For example, this migratory event elicits diminished epithelial barrier-function, a known functional deficit present in inflammatory bowel disease (Hawker et al., *Gastroenterology* 79:508–511 (1980). In addition, it has been described that PMN's, when exposed to conditions present in the intestinal lumen, produce a small molecular weight hydrophilic substance that effectively elicits electrogenic $Cl^-$ secretion (Nash et al., *J. Clin. Invest.* 87:1474–1477 (1991)), the transport event that relates to the clinical setting of secretory diarrhea. However, this neutrophil-derived secretagogue activity only occurs upon exposure of the apical membrane of intestinal epithelial cells (which would require transepithelial migration).

One factor impeding characterization of PMN transepithelial migration has been the lack of availability of a microassay system that circumvents the use of Ussing chambers and thus permits large numbers of parallel experiments to be performed. The present invention fills this need and can be utilized for studies of transmigration in either direction by either simple electrical or MPO assays.

Lastly, we report a distinct polarity to the efficacy of PMN migration across epithelia. An increase in available receptors due simply to surface area considerations is unlikely to explain the degree of enhanced efficiency of transmigration in the serosal-to-mucosal direction. However, factors other than differences in the biochemical composition/receptor density and/or type of apical and basolateral membranes play a role in determining the efficiency of migration. For example, when migrating in the serosal-to-mucosal direction, PMN's first encounter matrix components (those applied to the filter (type I collagen) and those synthesized by the epithelial cells), and it is known that PMN interactions with matrix can play a "priming" role in PMN functions such as the respiratory burst (Nathan et al., *J. Clin. Invest.* 80:1550–1560 (1987); and Nathan et al., *J. Cell Biol.* 109:1341–1349 (1989)).

The examples described above using NDS and the microassay are merely a few examples of the use of the present invention. Variations in the actual processes described in the examples will be apparent to those skilled in the art. Therefore, the present invention is to be considered limited only by the claims as follows.

What is claimed is:

1. An apparatus for assessing transmigration of polymorphonuclear leukocytes (PMN's) across epithelia in a serosal-to-mucosal direction, comprising:

(a) a culture plate having an upper surface and a plurality of individual wells, each well having an internal surface;

(b) at least one insert that is removably disposed within one of said wells of said culture plate, said insert comprising:

(i) a hollow cylinder having an open top end, an open bottom end having a bottom edge and an inner diameter, and an inner and an outer surface;

(ii) means for suspending said cylinder placed between said top end of said cylinder and said upper surface of said culture plate;

(iii) a filter having a first and second surface;

(iv) a layer of collagen as a viscous solution provided on said first surface of said filter whereby a cell monolayer can be grown on said layer of collagen;

(v) a ring having a side wall approximately the same diameter as said bottom end of said cylinder and having a top edge, said filter being attached to said bottom edge of said cylinder so that said second surface of said filter covers said open bottom end of said cylinder, said ring being attached to said bottom edge of said cylinder and said filter so that said side wall defines a volume for holding culture medium such that a cell monolayer can be grown on said layer of collagen;

(c) an internal serosal reservoir bound by said inner surface of said cylinder, and said second surface of said filter;

(d) an external mucosal reservoir bound by said inner surface of said well, said external surface of said cylinder, said ring, and said first surface of said filter;

(e) current means for passing current between said internal serosal reservoir and said external mucosal reservoir; and (f) recorder means for recording voltage between said internal serosal reservoir and said external mucosal reservoir.

2. The apparatus of claim 1, wherein there are at least three wells, each well including at least one insert.

3. The apparatus of claim 1, wherein said means for suspending said cylinder further comprises an annular lip having an inner side and an outer edge, said inner side of said annular lip being congruent with said inner surface of said top end of said cylinder, said outer edge of said annular lip being positioned on said upper surface of said culture plate whereby said insert is suspended in said well by said annular lip.

4. The apparatus of claim 1, wherein each surface of said first and second surfaces of said filter of said insert is about 0.33 cm².

5. The apparatus of claim 1, wherein said viscous solution comprises rat-tail collagen diluted 1:100 with 60% ethanol.

6. The apparatus of claim 1, wherein the current means for passing current comprises:

(a) a first Ag-AgCl electrode having a top and a bottom end disposed within said internal serosal reservoir above said second surface of said filter, and (b) a second Ag-AgCl electrode having a top end and a bottom end disposed within said external mucosal reservoir below said first surface of said filter, wherein each of said bottom ends of said Ag-AgCl electrodes is connected to an agar bridge.

7. The apparatus of claim 6, wherein said agar bridge comprises a 5% agar solution.

8. The apparatus of claim 1, wherein the recorder means for recording voltage comprises:

(a) a first calomel electrode having a top end and a bottom end disposed within said internal serosal reservoir above said second surface of said filter, and (b) a second calomel electrode having a top end and a bottom end disposed within said external mucosal reservoir below said first surface of said filter, wherein each of said bottom ends of said calomel electrodes is connected to an agar bridge.

9. The apparatus of claim 8, wherein said agar bridge comprises a 5% agar solution.

* * * * *